United States Patent
Bursulaya et al.

(10) Patent No.: US 8,178,526 B2
(45) Date of Patent: May 15, 2012

(54) COMPOUNDS AND COMPOSITIONS AS ITPKB INHIBITORS

(75) Inventors: Badry Bursulaya, San Diego, CA (US); Dai Cheng, San Diego, CA (US); Jiqing Jiang, San Diego, CA (US); Donald S. Karanewsky, Escondido, CA (US); Yi Liu, San Diego, CA (US); Shifeng Pan, San Diego, CA (US); Yongqin Wan, Irvine, CA (US); Xia Wang, San Diego, CA (US); Yun Feng Xie, San Diego, CA (US); Yang Yang, San Diego, CA (US)

(73) Assignee: IRM LLC, Hamilton (BM)

( * ) Notice: Subject to any disclaimer, the term of this patent is extended or adjusted under 35 U.S.C. 154(b) by 253 days.

(21) Appl. No.: 12/664,651

(22) PCT Filed: Jun. 12, 2008

(86) PCT No.: PCT/US2008/066664
§ 371 (c)(1),
(2), (4) Date: Feb. 5, 2010

(87) PCT Pub. No.: WO2008/157210
PCT Pub. Date: Dec. 24, 2008

(65) Prior Publication Data
US 2010/0184748 A1    Jul. 22, 2010

Related U.S. Application Data

(60) Provisional application No. 60/944,354, filed on Jun. 15, 2007.

(51) Int. Cl.
C07D 413/02    (2006.01)
C07D 413/14    (2006.01)
A61K 31/536    (2006.01)
A61K 31/551    (2006.01)

(52) U.S. Cl. ........... 514/230.5; 514/252.13; 514/253.05; 514/253.06; 544/92; 544/105; 544/359; 544/363

(58) Field of Classification Search .............. 544/92, 544/105, 359, 363; 514/230.5, 252.13, 253.05, 514/253.06
See application file for complete search history.

(56) References Cited

U.S. PATENT DOCUMENTS

| | | | |
|---|---|---|---|
| 5,624,941 A | 4/1997 | Barth et al. | |
| 6,114,334 A | 9/2000 | Kerrigan et al. | |
| 6,727,264 B1 | 4/2004 | Marzabadi et al. | |
| 7,803,831 B2 * | 9/2010 | Beswick et al. | 514/406 |

FOREIGN PATENT DOCUMENTS

| | | |
|---|---|---|
| WO | WO9413661 | 6/1994 |
| WO | WO9703067 | 1/1997 |
| WO | WO2004050087 | 6/2004 |
| WO | WO2004066926 | 8/2004 |
| WO | WO2004113330 | 12/2004 |
| WO | WO2005019182 | 3/2005 |
| WO | WO2008011611 | 1/2008 |

OTHER PUBLICATIONS

Database Chemcats [Online] 1-6 Chemi ca 1 Abstract Service, Columbus, Ohio, US; XP002461668 retrieved from STN Order Nos. HTS 05672, HTS 05430, HTS 05429, HTS 05426, HTS 05424, HTS 05419, HTS 05413, HTS 05411, HTS 05410 abstract, (Jul. 9, 2007).

* cited by examiner

*Primary Examiner* — Kahsay T Habte
(74) *Attorney, Agent, or Firm* — Daniel E. Raymond; Genomics Institute of the Novartis Research Foundation

(57) ABSTRACT

The invention provides a novel class of compounds of formula (I), pharmaceutical compositions comprising such compounds and methods of using such compounds to treat or prevent diseases or disorders associated with abnormal or dysregulated B cell activities, particularly diseases or disorders that involve aberrant activation of inositol 1,4,5-trisphosphate 3-kinase B (ITPKb).

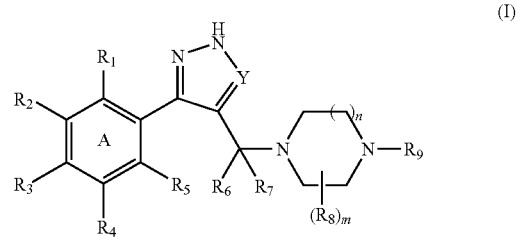

7 Claims, No Drawings

COMPOUNDS AND COMPOSITIONS AS ITPKB INHIBITORS

CROSS-REFERENCE TO RELATED APPLICATIONS

This application is a 371 U.S. national phase application of international application number PCT/US2008/066664 filed 12 Jun. 2008, which application claims priority to U.S. provisional patent application number 60/944,354, filed 15 Jun. 2007. The full disclosure of these applications is incorporated herein by reference in its entirety and for all purposes.

FIELD OF THE INVENTION

The invention provides a novel class of compounds, pharmaceutical compositions comprising such compounds and methods of using such compounds to treat or prevent diseases or disorders associated with abnormal or dysregulated B cell activities, particularly diseases or disorders that involve aberrant activation of inositol 1,4,5-trisphosphate 3-kinase B (ITPKb).

BACKGROUND

The protein kinases represent a large family of proteins, which play a central role in the regulation of a wide variety of cellular processes and maintaining control over cellular function. A partial, non-limiting, list of these kinases include: non-protein substrate kinases such as IPTKb; receptor tyrosine kinases such as platelet-derived growth factor receptor kinase (PDGF-R), the nerve growth factor receptor, trkB, Met, and the fibroblast growth factor receptor, FGFR3; non-receptor tyrosine kinases such Abl and the fusion kinase BCR-Abl, Lck, Csk, Fes, Bmx and c-src; and serine/threonine kinases such as b-RAF, c-RAF, sgk, MAP kinases (e.g., MKK4, MKK6, etc.) and SAPK2α, SAPK2β and SAPK3. Aberrant kinase activity has been observed in many disease states including benign and malignant proliferative disorders as well as diseases resulting from inappropriate activation of the immune and nervous systems.

The novel compounds of this invention inhibit the activity of ITPKb and are, therefore, expected to be useful in the treatment of ITPKb-associated diseases.

SUMMARY OF THE INVENTION

In one aspect, the present invention provides compounds of Formula I:

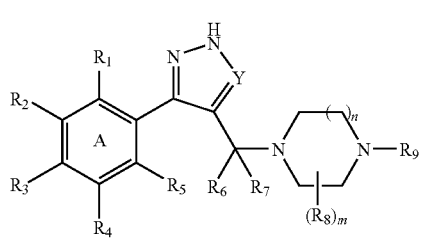

(I)

in which:
n is selected from 0, 1, 2 and 3;
m is selected from 0, 1, 2 and 3;
A can have up to 3 groups selected from —CR$_1$=, —CR$_2$= and —CR$_5$= replaced with —N=;

$R_1$, $R_2$ and $R_5$ are independently selected from hydrogen, hydroxy, halo, cyano, $C_{1-6}$alkyl, halo-substituted-$C_{1-6}$alkyl, hydroxy-substituted-$C_{1-6}$alkyl and cyano-substituted-$C_{1-6}$alkyl;

$R_3$ and $R_4$, together with the carbon atoms to which $R_3$ and $R_4$ are attached, form a 5 to 6 member heterocycle fused to ring A containing up to 4 radicals selected from O, C(O), S(O)$_2$, CR$_{11}$R$_{12}$ and NH; wherein each $R_{11}$ and $R_{12}$ are independently selected from hydrogen, $C_{1-3}$alkyl, and halo-substituted-$C_{1-3}$alkyl; or $R_{11}$ and $R_{12}$, together with the carbon to which they are both attached, forms $C_{3-7}$cycloalkyl;

$R_6$ and $R_7$ are independently selected from hydrogen, $C_{1-3}$alkyl and halo-substituted-$C_{1-3}$alkyl; or $R_6$ and $R_7$, together with the carbon to which they are both attached, forms $C_{3-7}$cycloalkyl;

$R_8$ is selected from $C_{1-6}$alkyl, $C_{2-6}$alkenyl, halo-substituted-$C_{1-6}$alkyl and hydroxy-substituted-$C_{1-6}$alkyl; or two $R_8$ groups can combine to form an alkyl bridge; or when two $R_8$ groups are attached to the same carbon atom, they, together with the carbon to which they are both attached, form $C_{3-7}$cycloalkyl;

$R_9$ is selected from $L_1$-$C_{6-10}$aryl, $L_1$-$C_{1-10}$heteroaryl, $C_{1-6}$alkyl, $L_1$-$C_{3-12}$cycloalkyl and $L_1$-$C_{3-8}$heterocycloalkyl; wherein said aryl, heteroaryl, cycloalkyl and heterocycloalkyl of $R_9$ can be optionally substituted with 1 to 3 radicals independently selected from halo, cyano, hydroxy, $C_{1-3}$alkyl, halo-substituted-$C_{1-3}$alkyl, cyano-substituted-$C_{1-3}$alkyl, hydroxy-substituted-$C_{1-3}$alkyl, —C(O)R$_{13}$, —C(O)NR$_{13}$R$_{14}$; wherein each $R_{13}$ and $R_{14}$ are independently selected from hydrogen and $C_{1-6}$alkyl;

$L_1$ is a bond, $C_{1-3}$alkyl or halo-substituted-$C_{1-3}$alkyl;
Y is N or CR$_{10}$;
$R_{10}$ is selected from hydrogen, $C_{1-6}$alkyl, —NR$_{15}$R$_{16}$, —NR$_{15}$C(O)R$_{16}$ and —C(O)NR$_{15}$R$_{16}$; wherein each $R_{15}$ and $R_{16}$ are independently selected from hydrogen, $C_{1-6}$alkyl, $C_{6-10}$aryl $C_{1-10}$heteroaryl, $C_{3-12}$cycloalkyl and $C_{3-8}$heterocycloalkyl; wherein said aryl, heteroaryl, cycloalkyl and heterocycloalkyl can be optionally substituted with 1 to 3 radicals independently selected from halo, hydroxy, cyano, $C_{1-6}$alkyl, halo-substituted-$C_{1-6}$alkyl, $C_{1-6}$alkoxy and halo-substituted-$C_{1-6}$alkoxy; and the N-oxide derivatives, prodrug derivatives, protected derivatives, individual isomers and mixture of isomers thereof;

and the pharmaceutically acceptable salts and solvates (e.g. hydrates) of such compounds.

In a second aspect, the present invention provides a pharmaceutical composition which contains a compound of Formula I or a N-oxide derivative, individual isomers and mixture of isomers thereof; or a pharmaceutically acceptable salt thereof, in admixture with one or more suitable excipients.

In a third aspect, the present invention provides a method of treating a disease in an animal in which inhibition of kinase activity, particularly ITPKb activity, can prevent, inhibit or ameliorate the pathology and/or symptomology of the diseases, which method comprises administering to the animal a therapeutically effective amount of a compound of Formula I or a N-oxide derivative, individual isomers and mixture of isomers thereof, or a pharmaceutically acceptable salt thereof.

In a fourth aspect, the present invention provides the use of a compound of Formula I in the manufacture of a medicament for treating a disease in an animal in which kinase activity, particularly ITPKb activity, contributes to the pathology and/or symptomology of the disease.

In a fifth aspect, the present invention provides a process for preparing compounds of Formula I and the N-oxide derivatives, prodrug derivatives, protected derivatives, individual isomers and mixture of isomers thereof, and the pharmaceutically acceptable salts thereof.

DETAILED DESCRIPTION OF THE INVENTION

Definitions

"Alkyl" as a group and as a structural element of other groups, for example halo-substituted-alkyl and alkoxy, can be either straight-chained or branched. $C_{1-4}$-alkoxy includes, methoxy, ethoxy, and the like. Halo-substituted alkyl includes trifluoromethyl, pentafluoroethyl, and the like. Hydroxy-substituted alkyl includes hydroxy-methyl, hydroxy-ethyl and the like.

"Aryl" means a monocyclic or fused bicyclic aromatic ring assembly containing six to ten ring carbon atoms. For example, aryl may be phenyl or naphthyl, preferably phenyl. "Arylene" means a divalent radical derived from an aryl group.

"Heteroaryl" is as defined for aryl above where one or more of the ring members can be a heteroatom selected from —O—, —N=, —NR—, —C(O)—, —S—, —S(O)— or —S(O)$_2$—, wherein R is hydrogen, $C_{1-4}$alkyl or a nitrogen protecting group. For example $C_{1-10}$heteroaryl includes pyridyl, indolyl, indazolyl, quinoxalinyl, quinolinyl, benzofuranyl, benzopyranyl, benzothiopyranyl, benzo[1,3]dioxole, imidazolyl, benzo-imidazolyl, pyrimidinyl, furanyl, oxazolyl, isoxazolyl, triazolyl, tetrazolyl, pyrazolyl, thienyl, etc.

"Cycloalkyl" means a saturated or partially unsaturated, monocyclic, fused bicyclic or bridged polycyclic ring assembly containing the number of ring atoms indicated. For example, $C_{3-10}$cycloalkyl includes cyclopropyl, cyclobutyl, cyclopentyl, cyclohexyl, etc.

"Heterocycloalkyl" means cycloalkyl, as defined in this application, provided that one or more of the ring carbons indicated, are replaced by a moiety selected from —O—, —N=, —NR—, —C(O)—, —S—, —S(O)— or —S(O)$_2$—, wherein R is hydrogen, $C_{1-4}$alkyl or a nitrogen protecting group. For example, $C_{3-8}$heterocycloalkyl as used in this application to describe compounds of the invention includes morpholino, pyrrolidinyl, pyrrolidinyl-2-one, piperazinyl, piperidinyl, piperidinylone, 1,4-dioxa-8-aza-spiro[4.5]dec-8-yl, etc.

"Halogen" (or halo) preferably represents chloro or fluoro, but may also be bromo or iodo.

"Treat", "treating" and "treatment" refer to a method of alleviating or abating a disease and/or its attendant symptoms.

DESCRIPTION OF THE PREFERRED EMBODIMENTS

The present invention provides compounds, compositions and methods for the treatment of kinase related disease, particularly IPTKb related diseases. For example, autoimmune diseases, particularly B cell associated diseases, are related to IPTKb. For example, rheumatoid arthritis, systemic lupus erythematosus (SLE), immune thrombocytopenic purpura (ITP) and hemolytic anemia.

In one embodiment, with reference to compounds of Formula I, n is selected from 1 and 2; m is selected from 0, 1 and 2; A can have up to 3 groups selected from —CR$_1$=, —CR$_2$= and —CR$_5$= replaced with N=; R$_1$, R$_2$ and R$_5$ are hydrogen; R$_6$ and R$_7$ are hydrogen; R$_8$ is selected from $C_{1-6}$alkyl, halo-substituted-$C_{1-6}$alkyl and hydroxy-substituted-$C_{1-6}$alkyl; or two R$_8$ groups can combine to form an alkyl bridge; or when two R$_8$ groups are attached to the same carbon, they, together with the carbon to which they are both attached, form $C_{3-7}$cycloalkyl; R$_9$ is selected from L$_1$-C$_{6-10}$aryl, L$_1$-C$_{1-10}$heteroaryl, C$_{1-6}$alkyl, L$_1$-C$_{3-12}$cycloalkyl and L$_1$-C$_{3-8}$heterocycloalkyl; wherein said aryl, heteroaryl, cycloalkyl and heterocycloalkyl of R$_9$ can be optionally substituted with 1 to 3 radicals independently selected from halo, cyano, hydroxy, $C_{1-3}$alkyl, halo-substituted-$C_{1-3}$alkyl, cyano-substituted-$C_{1-3}$alkyl, hydroxy-substituted-$C_{1-3}$alkyl, —C(O)R$_{13}$, —C(O)NR$_{13}$R$_{14}$; wherein each R$_{13}$ and R$_{14}$ are independently selected from hydrogen and $C_{1-6}$alkyl; L$_1$ is a bond or $C_{1-3}$alkyl; Y is CR$_{10}$, and R$_{10}$ is hydrogen.

In another embodiment, the 5 to 6 member heterocycle fused to ring A formed from R$_3$ and R$_4$, together with the carbon atoms to which R$_3$ and R$_4$ are attached, is selected from:

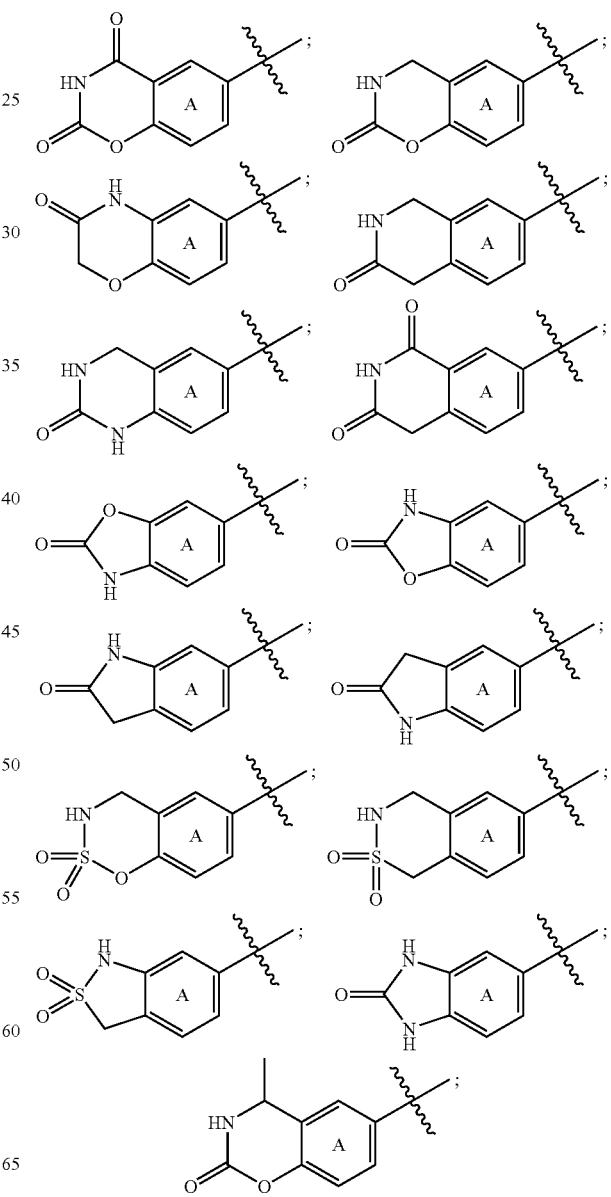

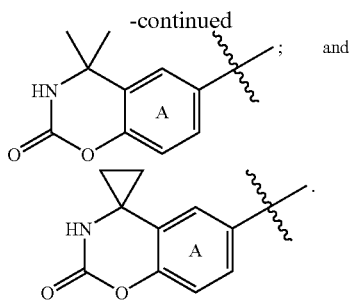

In another embodiment, $R_8$ is selected from methyl, ethyl, trifluoromethyl, difluoromethyl, fluoromethyl and hydroxymethyl; or two $R_8$ groups can combine to form an alkyl bridge selected from methyl, ethyl and propyl; or two $R_8$ groups are attached to the same carbon, they, together with the carbon to which they are both attached, form cyclopropyl.

In another embodiment, $R_9$ is selected from $C_{3-7}$cycloalkyl, $C_{4-7}$heterocycloalkyl, phenyl, pyridinyl, pyrazinyl, pyrimidinyl and furo[3,2-c]pyridin-4-yl; wherein said phenyl, pyridinyl, pyrazinyl, pyrimidinyl or furo[3,2-c]pyridin-4-yl is optionally substituted with 1 to 3 radicals independently selected from trifluoromethyl, cyano, bromo, chloro, hydroxy-methyl, methyl-carbonyl, methyl, amino-carbonyl, nitro, iodo, fluoro, methoxy-carbonyl, hydroxy, amino, carboxy and methoxy.

In another embodiment, are compounds selected from: 6-{4-[4-(5-Trifluoromethyl-pyridin-2-yl)-[1,4]diazepan-1-ylmethyl]-1H-pyrazol-3-yl}-benzo[e][1,3]oxazine-2,4-dione; 6-(4-((4-(5-(trifluoromethyl)pyridin-2-yl)piperazin-1-yl)methyl)-1H-pyrazol-3-yl)-3H-benzo[e][1,3]oxazine-2,4-dione; 6-(4-(((R)-4-(5-(trifluoromethyl)pyridin-2-yl)-3-methylpiperazin-1-yl)methyl)-1H-pyrazol-3-yl)-3H-benzo[e][1,3]oxazine-2,4-dione; 6-(4-(((S)-4-(5-(trifluoromethyl)pyridin-2-yl)-3-methylpiperazin-1-yl)methyl)-1H-pyrazol-3-yl)-3H-benzo[e][1,3]oxazine-2,4-dione; 6-(4-(((R)-4-(5-(trifluoromethyl)pyridin-2-yl)-3-methylpiperazin-1-yl)methyl)-1H-pyrazol-3-yl)-3,4-dihydrobenzo[e][1,3]oxazin-2-one; 6-(4-((4-(5-(trifluoromethyl)pyridin-2-yl)-1,4-diazepan-1-yl)methyl)-1H-pyrazol-3-yl)-3,4-dihydrobenzo[e][1,3]oxazin-2-one; 7-(4-(((R)-4-(5-(trifluoromethyl)pyridin-2-yl)-3-methylpiperazin-1-yl)methyl)-1H-pyrazol-3-yl)-1,2-dihydroisoquinolin-3(4H)-one; 7-(4-(((R)-4-(5-(trifluoromethyl)pyridin-2-yl)-3-methylpiperazin-1-yl)methyl)-1H-pyrazol-3-yl)isoquinoline-1,3(2H,4H)-dione; 6-(4-((4-(5-(trifluoromethyl)pyridin-2-yl)-1,4-diazepan-1-yl)methyl)-1H-pyrazol-3-yl)-3,4-dihydroquinazolin-2(1H)-one; 7-(4-((4-(5-(trifluoromethyl)pyridin-2-yl)-1,4-diazepan-1-yl)methyl)-1H-pyrazol-3-yl)-1,2-dihydroisoquinolin-3(4H)-one; and 6-(4-(((R)-4-(5-(trifluoromethyl)pyridin-2-yl)-3-methylpiperazin-1-yl)methyl)-1H-pyrazol-3-yl)-3,4-dihydroquinazolin-2(1H)-one; (R)-6-(4-((3-methyl-4-(5-(trifluoromethyl)pyridin-2-yl)piperazin-1-yl)methyl)-1H-pyrazol-3-yl)benzo[d]oxazol-2(3H)-one; 6-(4-((3-(trifluoromethyl)-4-(5-(trifluoromethyl)pyridin-2-yl)piperazin-1-yl)methyl)-1H-pyrazol-3-yl)-3,4-dihydro-2H-benzo[e][1,3]oxazin-2-one; 6-(4-((4-(5-(trifluoromethyl)pyridin-2-yl)piperazin-1-yl)methyl)-1H-pyrazol-3-yl)-3,4-dihydro-2H-benzo[e][1,3]oxazin-2-one; (R)-5-(4-((3-methyl-4-(5-(trifluoromethyl)pyridin-2-yl)piperazin-1-yl)methyl)-1H-pyrazol-3-yl)benzo[d]oxazol-2(3H)-one; 6-(4-((3-(5-(trifluoromethyl)pyridin-2-yl)-3,6-diazabicyclo[3.1.1]heptan-6-yl)methyl)-1H-pyrazol-3-yl)-3,4-dihydro-2H-benzo[e][1,3]oxazin-2-one; 6-(4-((2-(trifluoromethyl)-4-(5-(trifluoromethyl)pyridin-2-yl)piperazin-1-yl)methyl)-1H-pyrazol-3-yl)-3,4-dihydro-2H-benzo[e][1,3]oxazin-2-one; 6-(4-((3-(5-(trifluoromethyl)pyridin-2-yl)-3,8-diazabicyclo[3.2.1]octan-8-yl)methyl)-1H-pyrazol-3-yl)-3,4-dihydro-2H-benzo[e][1,3]oxazin-2-one; 6-(4-((3-(5-(trifluoromethyl)pyridin-2-yl)-3,8-diazabicyclo[3.2.1]octan-8-yl)methyl)-1H-pyrazol-3-yl)-2H-benzo[e][1,3]oxazine-2,4(3H)-dione; (S)-6-(4-((3-(fluoromethyl)-4-(5-(trifluoromethyl)pyridin-2-yl)piperazin-1-yl)methyl)-1H-pyrazol-3-yl)-3,4-dihydro-2H-benzo[e][1,3]oxazin-2-one; 6-(4-((4-(2,3-dimethylphenyl)piperazin-1-yl)methyl)-1H-pyrazol-3-yl)-2H-benzo[e][1,3]oxazine-2,4(3H)-dione; 6-(4-((4-(5-(trifluoromethyl)pyridin-2-yl)piperazin-1-yl)methyl)-1H-pyrazol-3-yl)-2H-benzo[b][1,4]oxazin-3(4H)-one; 6-(4-((4-(2,3-dimethylphenyl)piperazin-1-yl)methyl)-1H-pyrazol-3-yl)benzo[d]oxazol-2(3H)-one; (S)-6-(4-((3-(trifluoromethyl)-4-(5-(trifluoromethyl)pyridin-2-yl)piperazin-1-yl)methyl)-1H-pyrazol-3-yl)-3,4-dihydro-2H-benzo[e][1,3]oxazin-2-one; (R)-6-(4-((3-(trifluoromethyl)-4-(5-(trifluoromethyl)pyridin-2-yl)piperazin-1-yl)methyl)-1H-pyrazol-3-yl)-3,4-dihydro-2H-benzo[e][1,3]oxazin-2-one; (S)-6-(4-((3-(hydroxymethyl)-4-(5-(trifluoromethyl)pyridin-2-yl)piperazin-1-yl)methyl)-1H-pyrazol-3-yl)-3,4-dihydro-2H-benzo[e][1,3]oxazin-2-one; (R)-2-(2-methyl-4-((3-(2-oxo-3,4-dihydro-2H-benzo[e][1,3]oxazin-6-yl)-1H-pyrazol-4-yl)methyl)piperazin-1-yl)isonicotinonitrile; (R)-6-(4-((3-methyl-4-(4-(trifluoromethyl)pyrimidin-2-yl)piperazin-1-yl)methyl)-1H-pyrazol-3-yl)-3,4-dihydro-2H-benzo[e][1,3]oxazin-2-one; (R)-6-(4-((3-methyl-4-(5-methylpyridin-2-yl)piperazin-1-yl)methyl)-1H-pyrazol-3-yl)-3,4-dihydro-2H-benzo[e][1,3]oxazin-2-one; (S)-6-(4-((3-methyl-4-(5-(trifluoromethyl)pyridin-2-yl)piperazin-1-yl)methyl)-1H-pyrazol-3-yl)-3,4-dihydro-2H-benzo[e][1,3]oxazin-2-one; (R)-6-(4-((4-cyclohexyl-3-methylpiperazin-1-yl)methyl)-1H-pyrazol-3-yl)-3,4-dihydro-2H-benzo[e][1,3]oxazin-2-one; (R)-6-(5-((3-methyl-4-(5-(trifluoromethyl)pyridin-2-yl)piperazin-1-yl)methyl)-2H-1,2,3-triazol-4-yl)-3,4-dihydro-2H-benzo[e][1,3]oxazin-2-one; (R)-4,4-dimethyl-6-(4-((3-methyl-4-(5-(trifluoromethyl)pyridin-2-yl)piperazin-1-yl)methyl)-1H-pyrazol-3-yl)-3,4-dihydro-2H-benzo[e][1,3]oxazin-2-one; 6-(4-((4-(5-(trifluoromethyl)pyridin-2-yl)-4,7-diazaspiro[2.5]octan-7-yl)methyl)-1H-pyrazol-3-yl)-3,4-dihydro-2H-benzo[e][1,3]oxazin-2-one; (R)-6-(2-methyl-4-((3-(2-oxo-3,4-dihydro-2H-benzo[e][1,3]oxazin-6-yl)-1H-pyrazol-4-yl)methyl)piperazin-1-yl)nicotinonitrile; (R)-6-(4-((4-(5-chloropyridin-2-yl)-3-methylpiperazin-1-yl)methyl)-1H-pyrazol-3-yl)-3,4-dihydro-2H-benzo[e][1,3]oxazin-2-one; (S)-1-((3-(2-oxo-3,4-dihydro-2H-benzo[e][1,3]oxazin-6-yl)-1H-pyrazol-4-yl)methyl)-4-(5-(trifluoromethyl)pyridin-2-yl)piperazine-2-carboxylic acid; (S)-6-(4-((2-(hydroxymethyl)-4-(5-(trifluoromethyl)pyridin-2-yl)piperazin-1-yl)methyl)-1H-pyrazol-3-yl)-3,4-dihydro-2H-benzo[e][1,3]oxazin-2-one; (S)-6-(4-((2-(fluoromethyl)-4-(5-(trifluoromethyl)pyridin-2-yl)piperazin-1-yl)methyl)-1H-pyrazol-3-yl)-3,4-dihydro-2H-benzo[e][1,3]oxazin-2-one; (R)-6-(4-((3-methyl-4-(trifluoromethyl)phenyl)piperazin-1-yl)methyl)-1H-pyrazol-3-yl)-3,4-dihydro-2H-benzo[e][1,3]oxazin-2-one; (R)-6-(4-((2-fluorobenzyl)-3-methylpiperazin-1-yl)methyl)-1H-pyrazol-3-yl)-3,4-dihydro-2H-benzo[e][1,3]oxazin-2-one; (R)-6-(4-((4-(4-chlorophenyl)-3-methylpiperazin-1-yl)methyl)-1H-pyrazol-3-yl)-3,4-dihydro-2H-benzo[e][1,3]oxazin-2-one; (R)-6-(4-((3-methyl-4-(5-(trifluoromethyl)pyridin-2-yl)piperazin-1-yl)methyl)-1H-pyrazol-3-yl)-3,4-dihydro-2H-benzo[e][1,3]oxazin-2-one; (S)-6-(4-((3-methyl-4-(5-(trifluoromethyl)pyridin-2-yl)piperazin-1-yl)methyl)-1H-pyrazol-3-yl)-3,4-dihydro-2H-benzo[e][1,3]oxazin-2-one;

(S)-6-(4-((3-methyl-4-(5-(trifluoromethyl)pyridin-2-yl)piperazin-1-yl)methyl)-1H-pyrazol-3-yl)benzo[d]oxazol-2(3H)-one, (R)-6-(4-((3-methyl-4-(3-(trifluoromethyl)phenyl)piperazin-1-yl)methyl)-1H-pyrazol-3-yl)-3,4-dihydro-2H-benzo[e][1,3]oxazin-2-one, and (S)-6-(4-((4-cyclohexyl-3-methylpiperazin-1-yl)methyl)-1H-pyrazol-3-yl)-3,4-dihydro-2H-benzo[e][1,3]oxazin-2-one.

Further compounds of the invention are detailed in the Examples and Table I, infra.

Pharmacology and Utility

Compounds of the invention modulate the activity of IPTKb and, as such, are useful for treating diseases or disorders in which aberrant activity of IPTKb, contributes to the pathology and/or symptomology of diseases.

By inhibiting B cell activation and development, the ITPKb inhibitors of the present invention are useful in various therapeutic applications. Pharmacological inhibition of ITPKb provides a means to inhibit B cell malfunction in pathological settings. For example, B cells play a pathological role in chronic transplant rejection, and the development of autoimmune diseases (e.g. Rheumatoid Arthritis, SLE, lupus, and the like), Psoriasis, Allergy (Asthma, Rhinitis, COPD, Dermatitis) and others, including anaphylaxis and many complement mediated diseases. The ITPKb-inhibiting compounds of the invention can be effective agents to treat these diseases where ITPKb acts to promote pathogenesis.

Other diseases and conditions that are amenable to treatment include diseases associated with or mediated by abnormal B cell proliferation, e.g., B cell lymphoma. They also encompass other antibody-mediated disorders, e.g., allergies, psoriasis, systematic lupus erythematosus (SLE), primary binary cirrhosis (PBC), and idiopathic thrombocytopenic purpura (ITP). In addition to treating these diseases or conditions, ITPKb inhibitors of the present invention are also useful for preventing or modulating the development of such diseases or disorders in a subject (including human and animals such as other mammals) suspected of being, or known to be, prone to such diseases or disorders. The B-cell modulators that can be employed in the therapeutic applications of the invention include the specific ITPKb-inhibitors described in the Examples and tables, infra.

The invention thus provides a method for modulating B lymphocyte development and function in a subject (human or other mammal) for the treatment of autoimmune diseases, the method comprising administering to the subject a compound of formula I or a pharmaceutical composition thereof in an effective amount to modulate the kinase activity or cellular level of ITPKb (such as demonstrated by the in vitro assays described, infra); thereby modulating B lymphocyte differentiation and function in a subject. The compound can down-regulate the cellular level of the ITPKb molecule by inhibiting the kinase activity of ITPKb.

In accordance with the foregoing, the present invention further provides a method for preventing, treating and/or ameliorating the condition of any of the diseases or disorders described above in a subject in need of such treatment, which method comprises administering to said subject a therapeutically effective amount (See, "Administration and Pharmaceutical Compositions", infra) of a compound of Formula I or a pharmaceutically acceptable salt thereof. Compounds of Formula I can down-regulate the cellular level of the ITPKb molecule by inhibiting the kinase activity of ITPKb such as described by the in vitro assays described, infra. For any of the above uses, the required dosage will vary depending on the mode of administration, the particular condition to be treated and the effect desired.

Administration and Pharmaceutical Compositions

In general, compounds of the invention will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors. In general, satisfactory results are indicated to be obtained systemically at daily dosages of from about 0.03 to 2.5 mg/kg per body weight. An indicated daily dosage in the larger mammal, e.g. humans, is in the range from about 0.5 mg to about 100 mg, conveniently administered, e.g. in divided doses up to four times a day or in retard form. Suitable unit dosage forms for oral administration comprise from ca. 1 to 50 mg active ingredient.

Compounds of the invention can be administered as pharmaceutical compositions by any conventional route, in particular enterally, e.g., orally, e.g., in the form of tablets or capsules, or parenterally, e.g., in the form of injectable solutions or suspensions, topically, e.g., in the form of lotions, gels, ointments or creams, or in a nasal or suppository form. Pharmaceutical compositions comprising a compound of the present invention in free form or in a pharmaceutically acceptable salt form in association with at least one pharmaceutically acceptable carrier or diluent can be manufactured in a conventional manner by mixing, granulating or coating methods. For example, oral compositions can be tablets or gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrrolidone; if desired d) disintegrants, e.g., starches, agar, alginic acid or its sodium salt, or effervescent mixtures; and/or e) absorbents, colorants, flavors and sweeteners. Injectable compositions can be aqueous isotonic solutions or suspensions, and suppositories can be prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Suitable formulations for transdermal applications include an effective amount of a compound of the present invention with a carrier. A carrier can include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used. Suitable formulations for topical application, e.g., to the skin and eyes, are preferably aqueous solutions, ointments, creams or gels well-known in the art. Such may contain solubilizers, stabilizers, tonicity enhancing agents, buffers and preservatives.

Compounds of the invention can be administered in therapeutically effective amounts in combination with one or more therapeutic agents (pharmaceutical combinations). For example, synergistic effects can occur with other immunomodulatory or anti-inflammatory substances, for example when used in combination with cyclosporin, rapamycin, or ascomycin, or immunosuppressant analogues thereof, for example cyclosporin A (CsA), cyclosporin G, FK-506, rapamycin, or comparable compounds, corticosteroids, cyclophosphamide, azathioprine, methotrexate, brequinar, leflunomide, mizoribine, mycophenolic acid, mycophenolate mofetil, 15-deoxyspergualin, immunosuppressant antibodies, especially monoclonal antibodies for leukocyte receptors, for example MHC, CD2, CD3, CD4, CD7, CD25, CD28, B7, CD45, CD58 or their ligands, or other immunomodulatory compounds, such as CTLA4Ig. Where the compounds of the invention are administered in conjunction with other therapies, dosages of the co-administered compounds will of course vary depending on the type of co-drug employed, on the specific drug employed, on the condition being treated and so forth.

The invention also provides for a pharmaceutical combinations, e.g. a kit, comprising a) a first agent which is a compound of the invention as disclosed herein, in free form or in pharmaceutically acceptable salt form, and b) at least one co-agent. The kit can comprise instructions for its administration.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time.

The term "pharmaceutical combination" as used herein means a product that results from the mixing or combining of more than one active ingredient and includes both fixed and non-fixed combinations of the active ingredients. The term "fixed combination" means that the active ingredients, e.g. a compound of Formula I and a co-agent, are both administered to a patient simultaneously in the form of a single entity or dosage. The term "non-fixed combination" means that the active ingredients, e.g. a compound of Formula I and a co-agent, are both administered to a patient as separate entities either simultaneously, concurrently or sequentially with no specific time limits, wherein such administration provides therapeutically effective levels of the 2 compounds in the body of the patient. The latter also applies to cocktail therapy, e.g. the administration of 3 or more active ingredients.

Processes for Making Compounds of the Invention

The present invention also includes processes for the preparation of compounds of the invention. In the reactions described, it can be necessary to protect reactive functional groups, for example hydroxy, amino, imino, thio or carboxy groups, where these are desired in the final product, to avoid their unwanted participation in the reactions. Conventional protecting groups can be used in accordance with standard practice, for example, see T. W. Greene and P. G. M. Wuts in "Protective Groups in Organic Chemistry", John Wiley and Sons, 1991.

Compounds of Formula I, wherein $R_6$ and $R_7$ are both hydrogen, can be prepared by proceeding as in the following Reaction Scheme I:

Reaction Scheme I

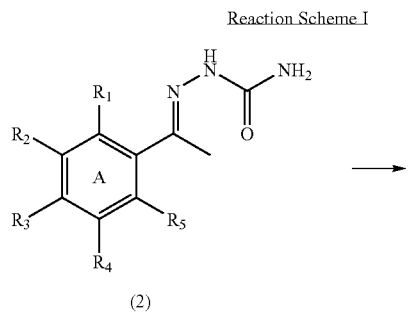

(2)

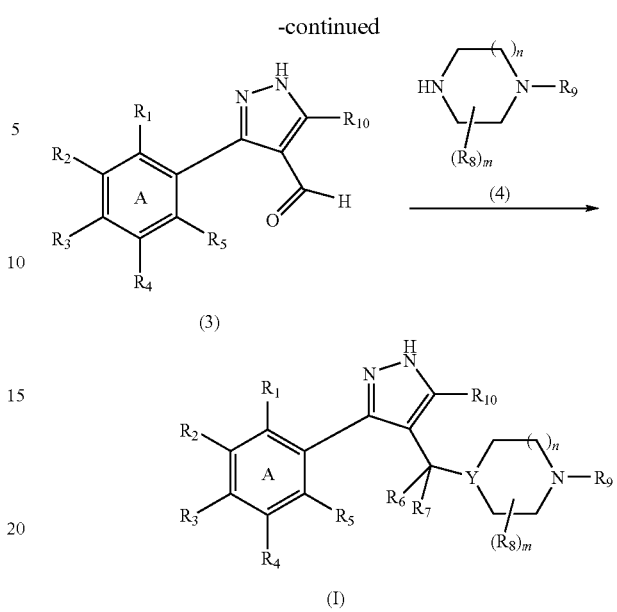

in which n, m, A, $R_1$, $R_2$, $R_3$, $R_4$, $R_5$, $R_8$, $R_9$ and $R_{10}$ are as defined in the Summary of the Invention.

A compound of Formula I can be prepared by reacting of a compound of formula 3 with a compound of formula 4 in the presence of a suitable solvent (e.g., DCM) using an appropriate reducing agents (e.g., NaCNBH$_3$). A compound of formula 3 can be prepared by reacting of a compound formula 2 with the complex of POCl$_3$ and DMF followed by the addition of a suitable base (e.g., NaOH).

Detailed examples of the synthesis of a compound of Formula I can be found in the Examples, infra.

Additional Processes for Making Compounds of the Invention

A compound of the invention can be prepared as a pharmaceutically acceptable acid addition salt by reacting the free base form of the compound with a pharmaceutically acceptable inorganic or organic acid. Alternatively, a pharmaceutically acceptable base addition salt of a compound of the invention can be prepared by reacting the free acid form of the compound with a pharmaceutically acceptable inorganic or organic base.

Alternatively, the salt forms of the compounds of the invention can be prepared using salts of the starting materials or intermediates.

The free acid or free base forms of the compounds of the invention can be prepared from the corresponding base addition salt or acid addition salt from, respectively. For example a compound of the invention in an acid addition salt form can be converted to the corresponding free base by treating with a suitable base (e.g., ammonium hydroxide solution, sodium hydroxide, and the like). A compound of the invention in a base addition salt form can be converted to the corresponding free acid by treating with a suitable acid (e.g., hydrochloric acid, etc.).

Compounds of the invention in unoxidized form can be prepared from N-oxides of compounds of the invention by treating with a reducing agent (e.g., sulfur, sulfur dioxide, triphenyl phosphine, lithium borohydride, sodium borohydride, phosphorus trichloride, tribromide, or the like) in a suitable inert organic solvent (e.g. acetonitrile, ethanol, aqueous dioxane, or the like) at 0 to 80° C.

Prodrug derivatives of the compounds of the invention can be prepared by methods known to those of ordinary skill in the art (e.g., for further details see Saulnier et al., (1994), Bioorganic and Medicinal Chemistry Letters, Vol. 4, p. 1985). For example, appropriate prodrugs can be prepared by reacting a non-derivatized compound of the invention with a suitable carbamylating agent (e.g., 1,1-acyloxyalkylcarbanochloridate, para-nitrophenyl carbonate, or the like).

Protected derivatives of the compounds of the invention can be made by means known to those of ordinary skill in the art. A detailed description of techniques applicable to the creation of protecting groups and their removal can be found in T. W. Greene, "Protecting Groups in Organic Chemistry", $3^{rd}$ edition, John Wiley and Sons, Inc., 1999.

Compounds of the present invention can be conveniently prepared, or formed during the process of the invention, as solvates (e.g., hydrates). Hydrates of compounds of the present invention can be conveniently prepared by recrystallization from an aqueous/organic solvent mixture, using organic solvents such as dioxin, tetrahydrofuran or methanol.

Compounds of the invention can be prepared as their individual stereoisomers by reacting a racemic mixture of the compound with an optically active resolving agent to form a pair of diastereoisomeric compounds, separating the diastereomers and recovering the optically pure enantiomers. While resolution of enantiomers can be carried out using covalent diastereomeric derivatives of the compounds of the invention, dissociable complexes are preferred (e.g., crystalline diastereomeric salts). Diastereomers have distinct physical properties (e.g., melting points, boiling points, solubilities, reactivity, etc.) and can be readily separated by taking advantage of these dissimilarities. The diastereomers can be separated by chromatography, or preferably, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques, Andre Collet, Samuel H. Wilen, "Enantiomers, Racemates and Resolutions", John Wiley And Sons, Inc., 1981.

In summary, the compounds of Formula I can be made by a process, which involves:

(a) that of reaction scheme I; and
(b) optionally converting a compound of the invention into a pharmaceutically acceptable salt;
(c) optionally converting a salt form of a compound of the invention to a non-salt form;
(d) optionally converting an unoxidized form of a compound of the invention into a pharmaceutically acceptable N-oxide;
(e) optionally converting an N-oxide form of a compound of the invention to its unoxidized form;
(f) optionally resolving an individual isomer of a compound of the invention from a mixture of isomers;
(g) optionally converting a non-derivatized compound of the invention into a pharmaceutically acceptable prodrug derivative; and
(h) optionally converting a prodrug derivative of a compound of the invention to its non-derivatized form.

The present invention also includes all suitable isotopic variations of the compounds of the invention, or pharmaceutically acceptable salts thereof. An isotopic variation of a compound of the invention or a pharmaceutically acceptable salt thereof is defined as one in which at least one atom is replaced by an atom having the same atomic number but an atomic mass different from the atomic mass usually found in nature. Examples of isotopes that may be incorporated into the compounds of the invention and pharmaceutically acceptable salts thereof include but are not limited to isotopes of hydrogen, carbon, nitrogen and oxygen such as $^2$H, $^3$H, $^{11}$C, $^{13}$C, $^{14}$C, $^{15}$N, $^{17}$O, $^{18}$O, $^{35}$S, $^{18}$F, $^{36}$Cl and $^{123}$I. Certain isotopic variations of the compounds of the invention and pharmaceutically acceptable salts thereof, for example, those in which a radioactive isotope such as $^3$H or $^{14}$C is incorporated, are useful in drug and/or substrate tissue distribution studies. In particular examples, $^3$H and $^{14}$C isotopes may be used for their ease of preparation and detectability. In other examples, substitution with isotopes such as $^2$H may afford certain therapeutic advantages resulting from greater metabolic stability, such as increased in vivo half-life or reduced dosage requirements. Isotopic variations of the compounds of the invention or pharmaceutically acceptable salts thereof can generally be prepared by conventional procedures using appropriate isotopic variations of suitable reagents. Isotopic variations of the compounds have the potential to change a compound's metabolic fate and/or create small changes in physical properties such as hydrophobicity, and the like. Isotopic variation have the potential to enhance efficacy and safety, enhance bioavailability and half-life, alter protein binding, change biodistribution, increase the proportion of active metabolites and/or decrease the formation of reactive or toxic metabolites.

Insofar as the production of the starting materials is not particularly described, the compounds are known or can be prepared analogously to methods known in the art or as disclosed in the Examples hereinafter.

One of skill in the art will appreciate that the above transformations are only representative of methods for preparation of the compounds of the present invention, and that other well known methods can similarly be used.

EXAMPLES

The present invention is further exemplified, but not limited, by the following examples that illustrate the preparation of compounds of Formula I according to the invention.

Example 1

6-{4-[4-(5-Trifluoromethyl-pyridin-2-yl)-[1,4]diazepan-1-ylmethyl]-1H-pyrazol-3-yl}-benzo[e][1,3]oxazine-2,4-dione

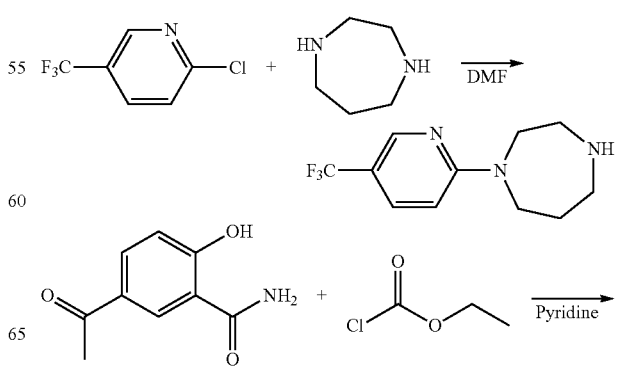

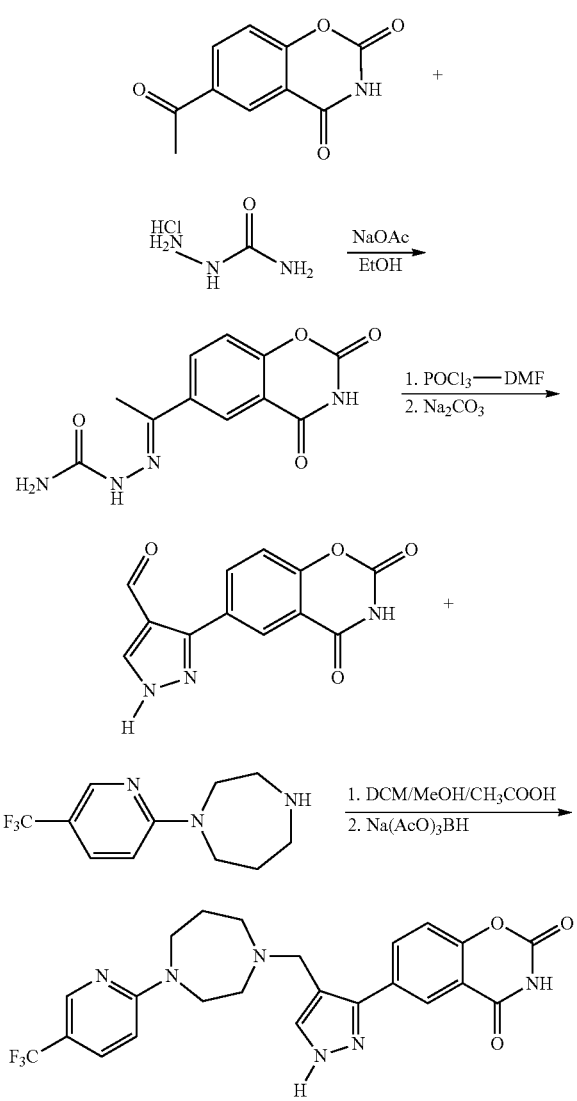

A mixture of 2-chloro-5-trifluoromethylpyridine (362 mg, 1.99 mmol) and [1,4]-diazepane (1000 mg, 9.98 mmol) in DMF (6.0 mL) is stirred for 2 hours at room temperature followed by evaporation of the solvent DMF under vacuo. The residue is distributed between ethyl acetate (30 mL) and water (40 mL). The aqueous phase is extracted once with ethyl acetate (20 m) and the combined organic phases are dried with Na₂SO₄. Evaporation gives an oily residue (crude 1-(5-trifluoromethyl-pyridin-2-yl)-[1,4]-diazepane) which is used directly for reductive amination in the last step.

To the suspension of 5-acetylsalicylamide (900 mg, 5.02 mmol) in pyridine (3.5 mL) at 0° C. under stirring is added ethyl chloro-carbamate (600 mg, 5.53 mmol) dropwise and the reaction is heated at 98° C. overnight. Pyridine is evaporated and the residue is distributed between ethyl acetate (100 mL) and water (60 mL). The organic phase is washed with HCl (2N, 50 mL) and water (60 mL) and dried with Na₂SO₄. As the organic phase is evaporated, the product 6-acetyl-benzo[e][1,3]oxazine-2,4-dione starts to precipitate. The precipitate is collected by filtration and then further concentrated until the starting material (5-acetylsalicylamide) begins to co-crystallize.

To a suspension of 6-acetyl-benzo[e][1,3]oxazine-2,4-dione (626 mg, 3.05 mmol) obtained above in ethanol (5.0 mL), is added a solution of NaOAc.3H₂O (910 mg, 2.2 equiv.) and semicarbazide hydrochloride (408 mg, 1.20 equiv.) in water (5.0 mL). The mixture is heated at 92° C. for 2 hours. After cooling to room temperature, the product is collected by filtration, washed with acetonitrile and dried under vacuum to give the corresponding semicarbazone derivative.

To anhydrous DMF (2.50 mL) at 0° C. under argon is added POCl₃ (0.60 mL, 1.01 g, 6.56 mmol) dropwise. After 10 minutes, the ice-bath is removed to allow the temperature to rise to room temperature. The semicarbazone obtained above is added in portions and the temperature is raised to and kept at 68° C. for 1 hour. The reaction is quenched into ice/water. Na₂CO₃ is used to raise the pH to about 11-12 followed by neutralization with NH₄Cl saturated aqueous solution. The precipitate is collected by filtration and dried in vacuum to give 3-(2,4-dioxo-3,4-dihydro-2H-benzo[e][1,3]oxazin-6-yl)-1H-pyrazole-4-carbaldehyde.

The mixture of 3-(2,4-dioxo-3,4-dihydro-2H-benzo[e][1,3]oxazin-6-yl)-1H-pyrazole-4-carbaldehyde (51.4 mg, 0.2 mmol) and 1-(5-trifluoromethyl-pyridin-2-yl)-[1,4]diazepane (24.5 mg, 0.1 mmol) in methylene chloride (1.0 mL), methanol (0.5 mL) and acetic acid (15 μL) is stirred for 30 minutes at room temperature. Then Na(AcO)₃BH (84 mg, 4.0 equiv.) is added and the reaction is stirred overnight at room temperature. After evaporation, the residue is redissolved in DMF (1.0 mL) which is subject to reverse-phase preparative LC-MS (acetonitrile/water/TFA gradient 10-90% CH₃CN in 7.5 min, Ultro 120 5 uM C18Q, 75×30 mmID) The collected water/MeCN solution of the TFA salt of the product is evaporated to remove the acetonitrile. A saturated aqueous solution of NaHCO₃ is added to raise the pH to about 8-9. Then ethyl acetate is used to extract the product and the organic phase is dried with Na₂SO₄. Evaporation of the solvent yields the free-based 6-{4-[4-(5-trifluoromethyl-pyridin-2-yl)-[1,4]diazepan-1-ylmethyl]-1H-pyrazol-3-yl}-benzo[e][1,3]oxazine-2,4-dione.

Example 2

6-(5-(((R)-4-(5-(trifluoromethyl)pyridin-2-yl)-3-methylpiperazin-1-yl)methyl)-2H-1,2,3-triazol-4-yl)-3,4-dihydrobenzo[e][1,3]oxazin-2-one

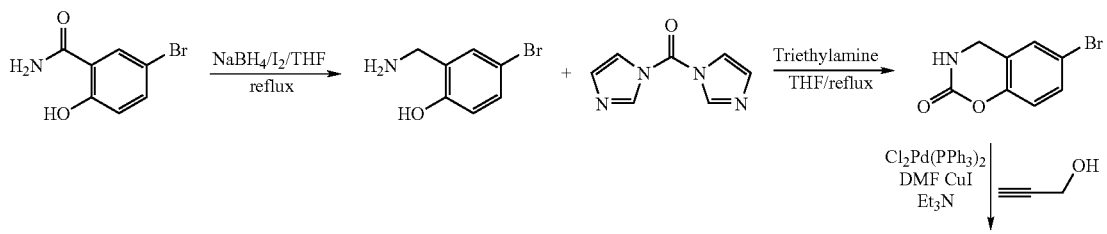

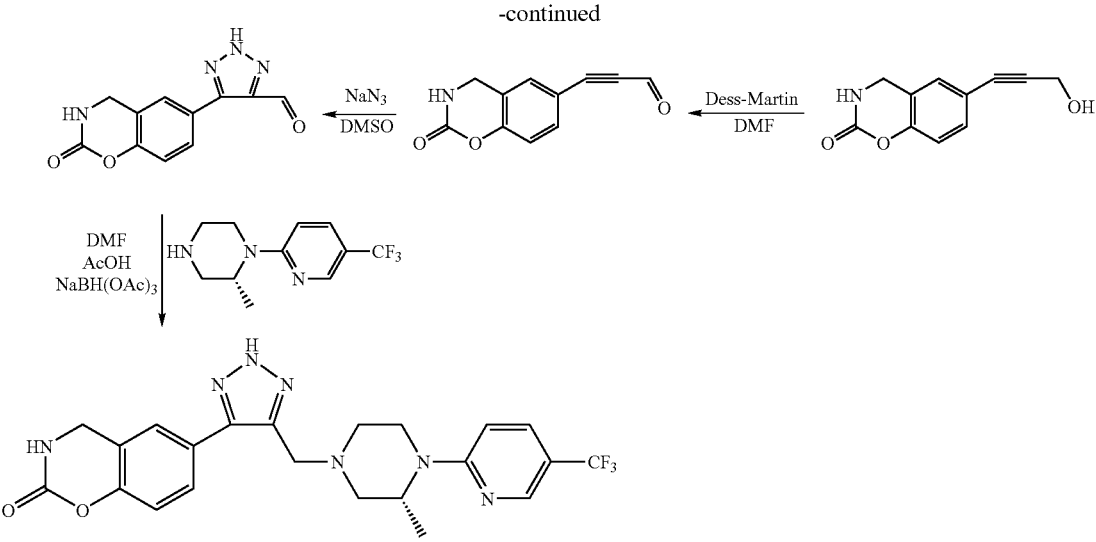

Example 2-1

Preparation of 2-(aminomethyl)-4-bromophenol

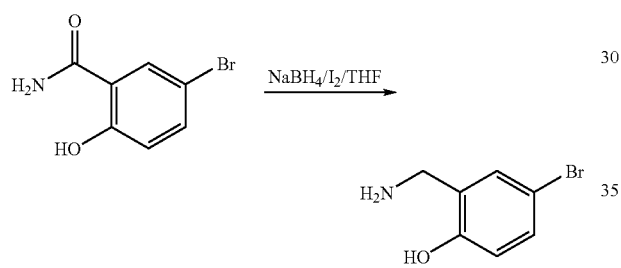

5-bromo-2-hydroxybenzamide (2.16 g, 10 mol) and NaBH$_4$ (1.52 g, 40 mol) are dissolved in dry THF (150 ml) in a two-neck septum capped round-bottom flask. Iodine (5.06 g, 20 mol)) in dry THF is added under nitrogen atmosphere at 0° C. over 2.5 hours. The reaction mixture is refluxed for 3 hours and then cooled to 0° C. The excess hydride is destroyed by careful addition of 1N HCl. After removing most organic solvent by vacuum, the acidic aqueous solution is diluted in 1N HCl (150 ml) and washed three times with ether (30 ml each time). The pH of the aqueous solution is adjusted to pH=6-7 by careful addition of sodium bicarbonate solid. The product is collected by filtration and then washed with water. The product is further dried in vacuum oven overnight giving 2-(aminomethyl)-4-bromophenol which is used directly in the next step without further purification.

Example 2-2

Preparation of 6-bromo-3,4-dihydrobenzo[e][1,3]oxazin-2-one

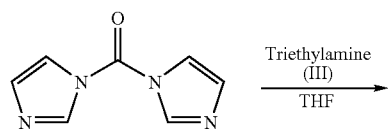

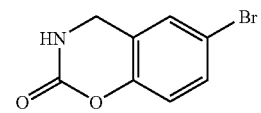

A solution of 2-(aminomethyl)-4-bromophenol (I) (1.16 g, 5.7 mmol), triethylamthylamine (III) and carbonyldiimidazole (II) (1.86 g, 11.5 mmol) in anhydrous THF (100 ml) is refluxed for 4 hours. The solvent is evaporated and the residue dissolved in dichloromethane (DCM) (100 ml). The organic solution is washed with 1N HCl (20 ml×3) and then with brine (50 ml). The solvent is then evaporated and the resulting residue is purified by chromatography to give 6-bromo-3,4-dihydrobenzo[e][1,3]oxazin-2-one as a white powder.

Example 2-3

Preparation of 3,4-dihydro-6-(3-hydroxyprop-1-ynyl)benzo[e][1,3]oxazin-2-one

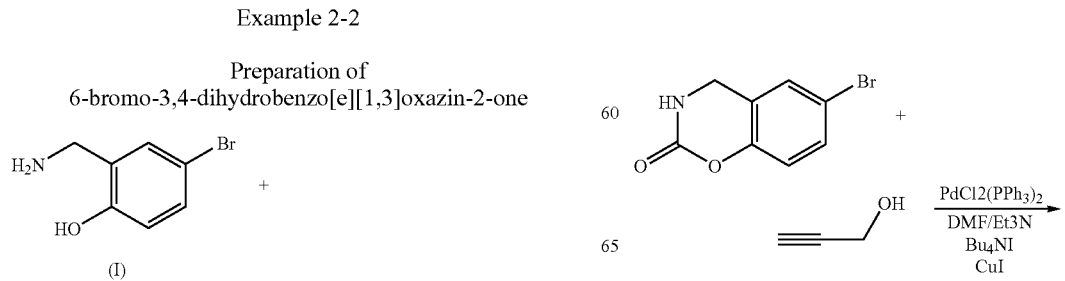

-continued

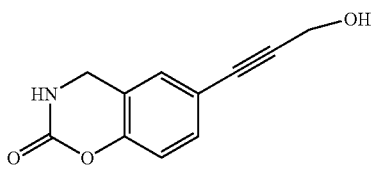

To a solution of 6-bromo-3,4-dihydrobenzo[e][1,3]oxazin-2-one (114 mg, 0.5 mmol), PdCl$_2$(PPh$_3$)$_2$ (60 mg, 0.05 mmol), CuI (20 mg, 0.1 mmol), tetrabutylammonium iodide (74 mg, 0.2 mmol) in 1 mL of DMF are added prop-2-yn-1-ol (150 mg, 2.5 mmol) and triethylamine (0.8 mL) via syringe under nitrogen atmosphere. The resultant mixture is heated at 75° C. until the aryl bromide is consumed, as monitored by TLC. The cooled solution is partitioned between ethyl acetate and water, and the organic layer is then washed with brine, and dried over Na$_2$SO$_4$. Evaporation of the solution followed by column chromatography afforded the coupling product: 3,4-dihydro-6-(3-hydroxyprop-1-ynyl)benzo[e][1,3]oxazin-2-one as colorless oil. m/e: 204 (M+1)

Example 2-4

Preparation of 5-(3,4-dihydro-2-oxo-2H-benzo[e][1,3]oxazin-6-yl)-2H-1,2,3-triazole-4-carbaldehyde

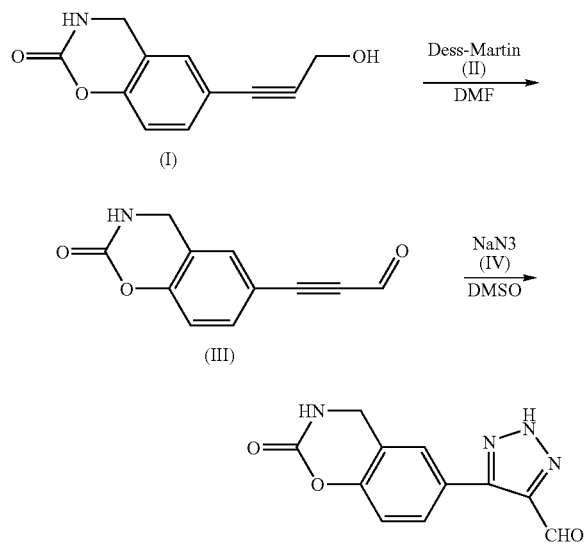

3,4-dihydro-6-(3-hydroxyprop-1-ynyl)benzo[e][1,3]oxazin-2-one (30 mg, 0.15 mmol) is dissolved in dimethyl formamide (DMF) (2 ml) and is treated with Dess-Martin reagent (130 mg, 0.3 mmol) at room temperature. After stirring for 1 hour, the reaction is quenched with 1N HCl (10 ml) and then extracted with ethyl acetate (EtOAc) (10 ml×5). The combined organic phase is washed with water, then saturated aqueous ammonia chloride, and then brine. After drying over sodium sulfate, the solvent is removed by vacuum to give crude aldehyde which is used directly in the next step.

The crude aldehyde obtained above is dissolved in DMSO (2 ml) and then treated with sodium azide (98 mg, 1.5 mmol) at room temperature. After stirring for 4 hours, the reaction is quenched with aqueous sodium bicarbonate solution (10 ml) and then extracted with EtOAc (10 ml×5). The combined organic phase is washed with water, then saturated aqueous sodium bicarbonate, and then brine. After drying over sodium sulfate, the solvent is removed by vacuum to give the crude product which is then purified by flash chromatography yielding 5-(3,4-dihydro-2-oxo-2H-benzo[e][1,3]oxazin-6-yl)-2H-1,2,3-triazole-4-carbaldehyde as a colorless oil. m/e: 245 (M+1).

Example 2-5

Preparation of 6-(5-(((R)-4-(5-(trifluoromethyl)pyridin-2-yl)-3-methylpiperazin-1-yl)methyl)-2H-1,2,3-triazol-4-yl)-3,4-dihydrobenzo[e][1,3]oxazin-2-one

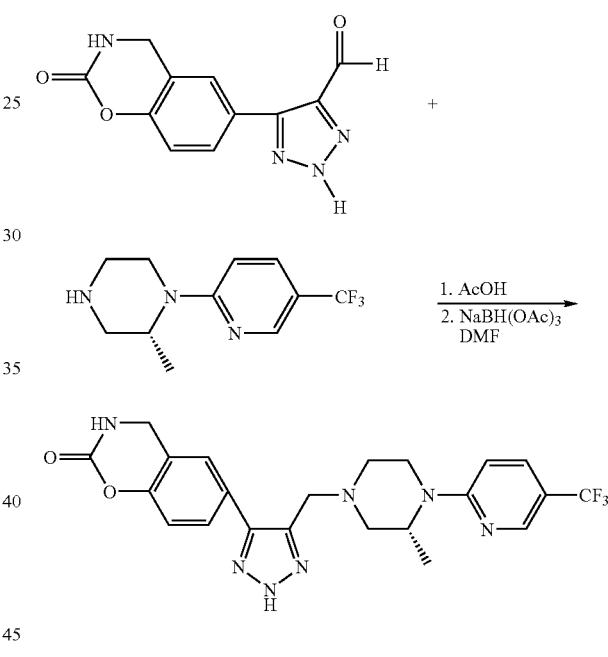

5-(3,4-dihydro-2-oxo-2H-benzo[e][1,3]oxazin-6-yl)-2H-1,2,3-triazole-4-carbaldehyde (15 mg, 0.06 mmol) and (R)-1-(5-(trifluoromethyl)pyridin-2-yl)-2-methylpiperazine (20 mg, 0.08 mmol) are mixed in DMF (1 ml) followed by addition of acetic acid (AcOH) (30 ul). The mixture is stirred at room temperature for 30 minute and then sodium triacetate boron hydride (42 mg, 0.2 mmol) is added. The resulting suspension is then stirred at room temperature overnight. The reaction is quenched using an aqueous saturated solution of sodium bicarbonate and then extracted with ethyl acetate (10 ml×4). The combined organic phase is concentrated and the resulting crude product is purified by HPLC giving 6-(5-(((R)-4-(5-(trifluoromethyl)pyridin-2-yl)-3-methylpiperazin-1-yl)methyl)-2H-1,2,3-triazol-4-yl)-3,4-dihydrobenzo[e][1,3]oxazin-2-one as a white powder. m/e:474 (M+1).

By repeating the procedures described in the above example, using appropriate starting materials, the following compounds of Formula I, as identified in Table 1, are obtained.

TABLE 1

| Compound Number | Structure | Physical Data MS (m/z): (M + 1) |
|---|---|---|
| 2 | 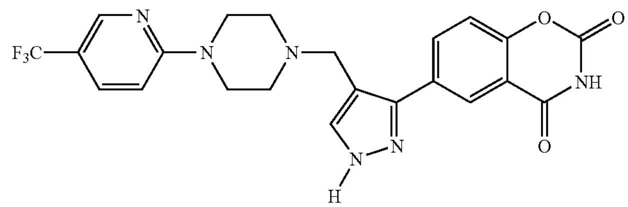 | 473.2 |
| 3 | 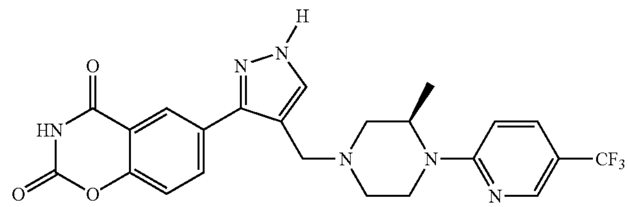 | 487.2 |
| 4 | 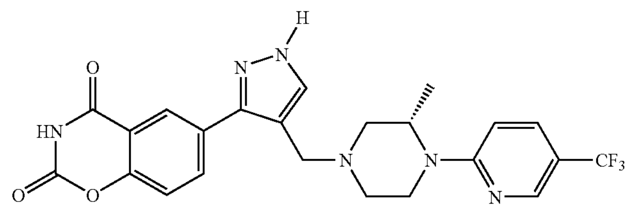 | 487.2 |
| 5 | 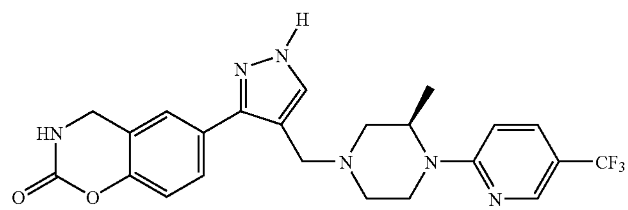 | 473.2 |
| 6 | 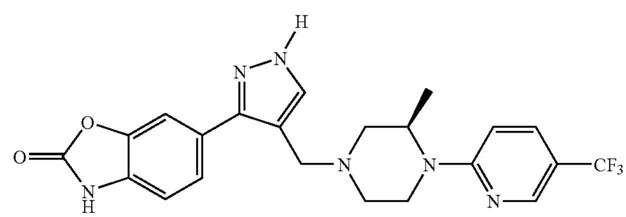 | 459.2 |
| 7 | 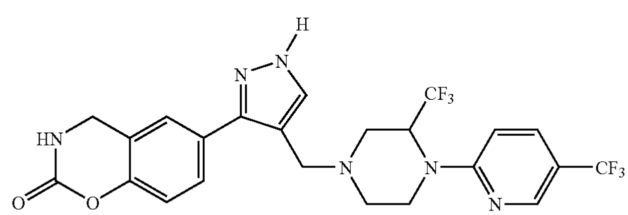 | 527.2 |
| 8 | 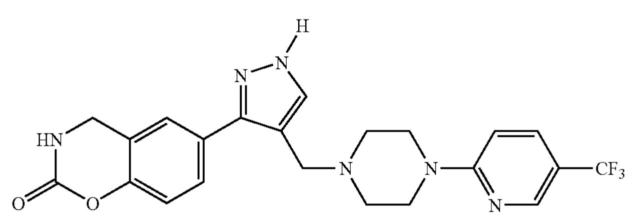 | 459.2 |

TABLE 1-continued

| Compound Number | Structure | Physical Data MS (m/z): (M + 1) |
|---|---|---|
| 9 | 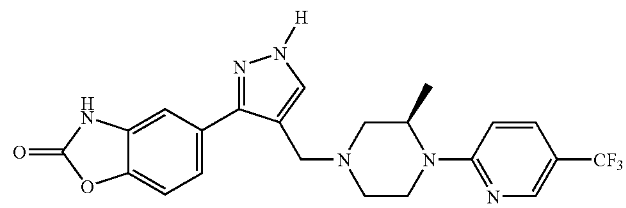 | 459.2 |
| 10 | 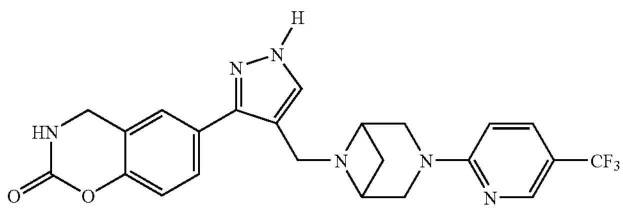 | 471.2 |
| 11 | 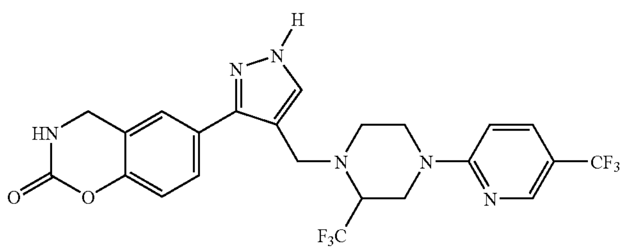 | 527.2 |
| 12 | 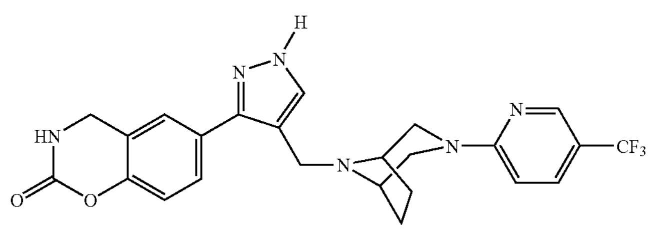 | 485.2 |
| 13 | 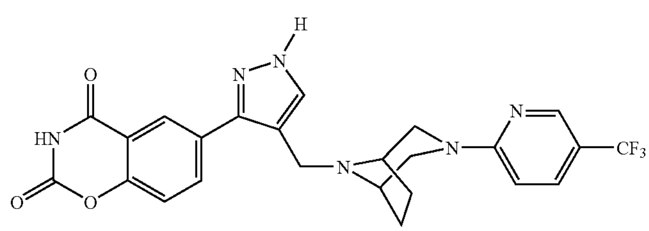 | 499.2 |
| 14 | 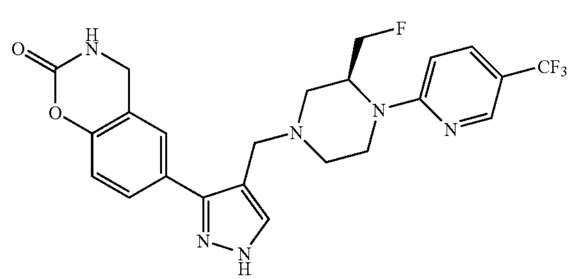 | 491.2 |

TABLE 1-continued
| Compound Number | Structure | Physical Data MS (m/z): (M + 1) |
|---|---|---|
| 15 | 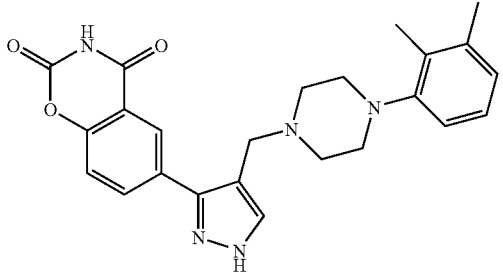 | 432.2 |
| 16 | 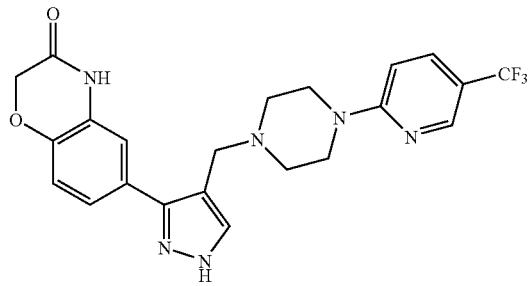 | 459.2 |
| 17 | 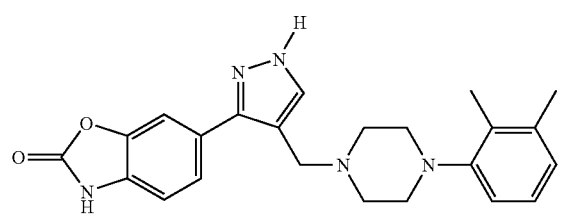 | 404.2 |
| 18 | 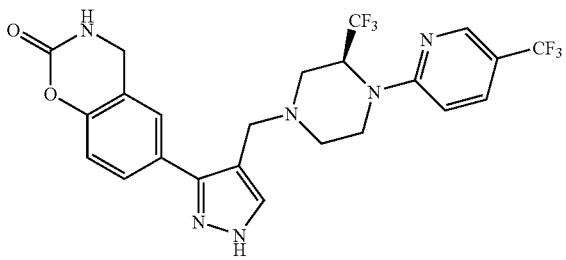 | 527.2 |
| 19 | 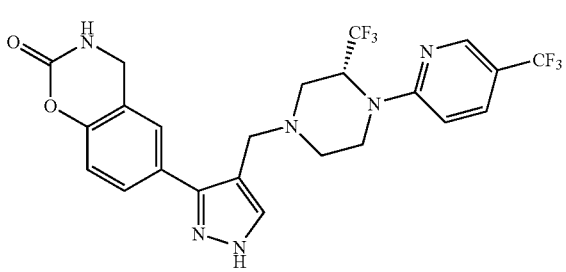 | 527.2 |

TABLE 1-continued

| Compound Number | Structure | Physical Data MS (m/z): (M + 1) |
|---|---|---|
| 20 | 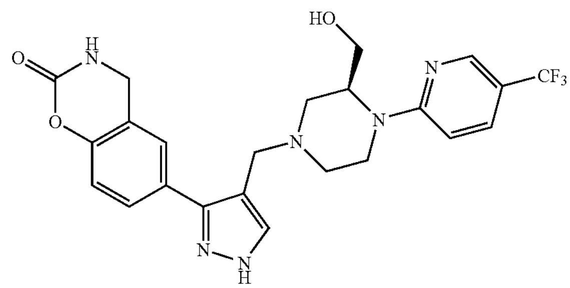 | 489.2 |
| 21 | 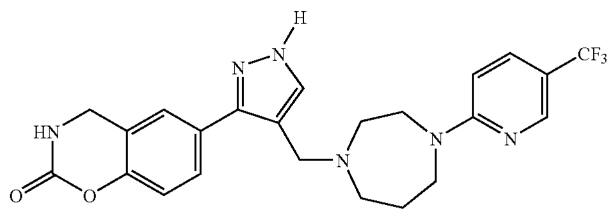 | |
| 22 | 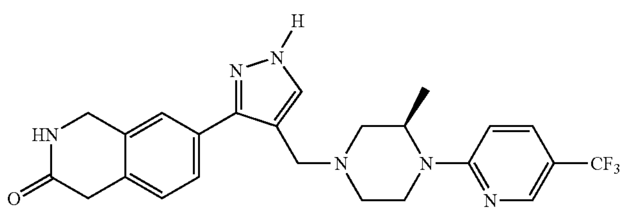 | |
| 23 | 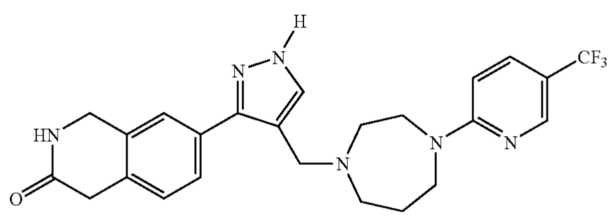 | |
| 24 | 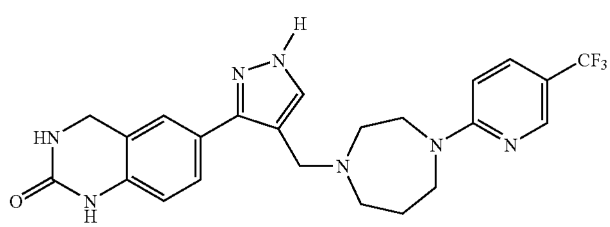 | |
| 25 | 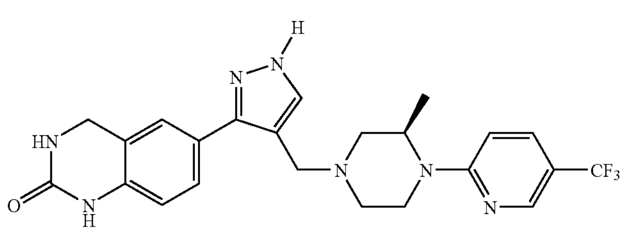 | |

TABLE 1-continued
| Compound Number | Structure | Physical Data MS (m/z): (M + 1) |
|---|---|---|
| 26 | 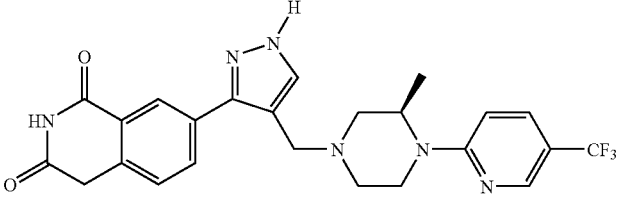 | |
| 27 | 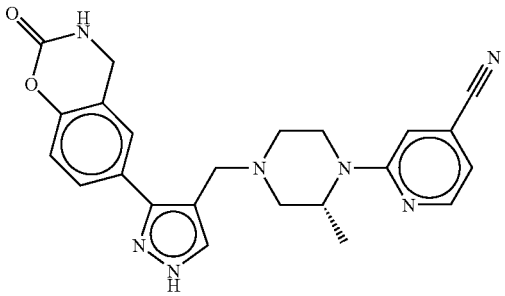 | 430.2 |
| 28 | 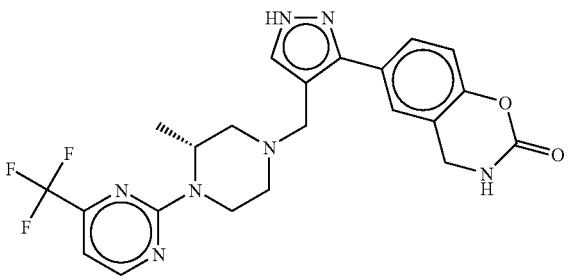 | 474.2 |
| 29 | 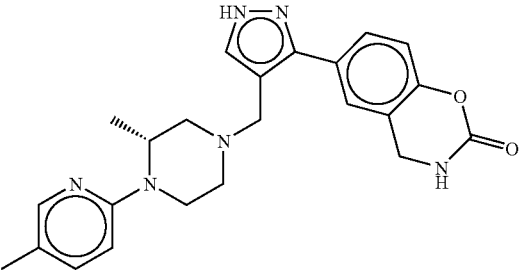 | 419.2 |
| 30 | 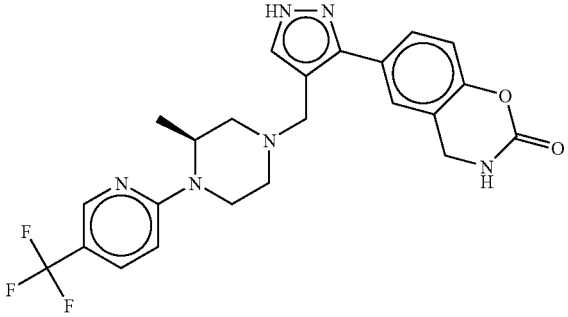 | 473.2 |

TABLE 1-continued
| Compound Number | Structure | Physical Data MS (m/z): (M + 1) |
|---|---|---|
| 31 | 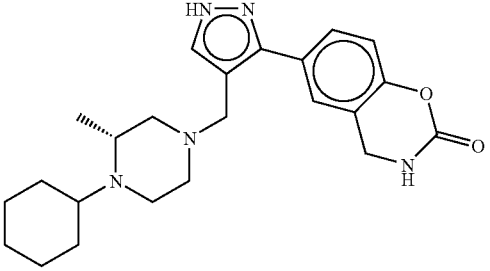 | 410.3 |
| 32 | 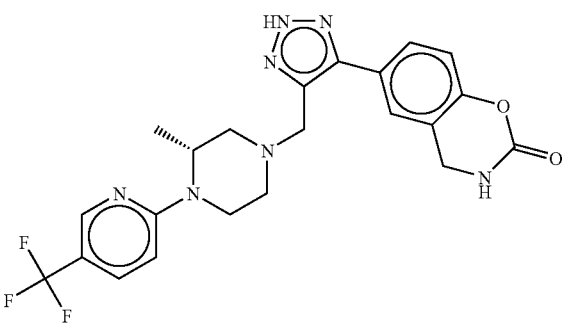 | 474.2 |
| 33 | 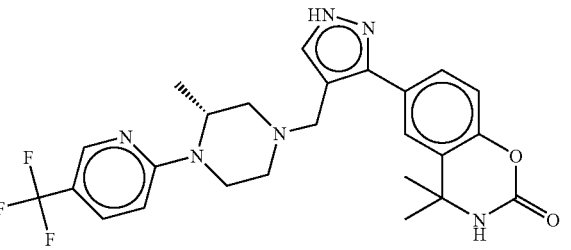 | 501.2 |
| 34 | 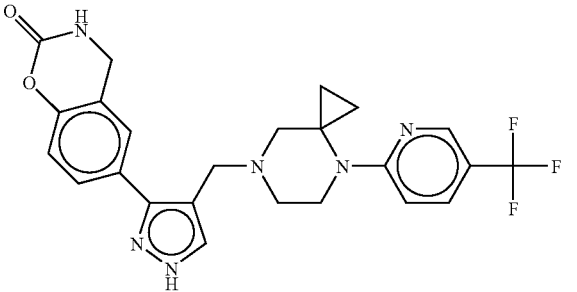 | 485.2 |
| 35 | 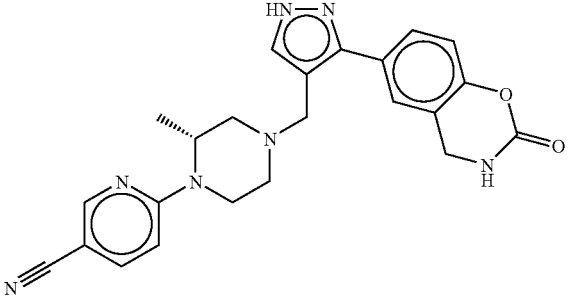 | 430.2 |

TABLE 1-continued

| Compound Number | Structure | Physical Data MS (m/z): (M + 1) |
|---|---|---|
| 36 | 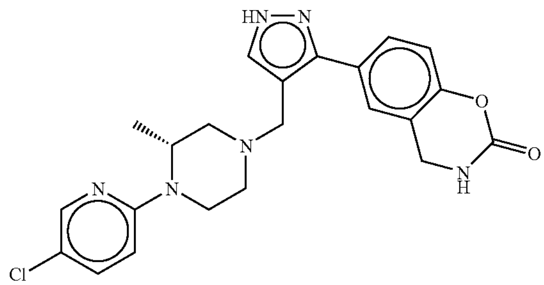 | 439.2 |
| 37 | 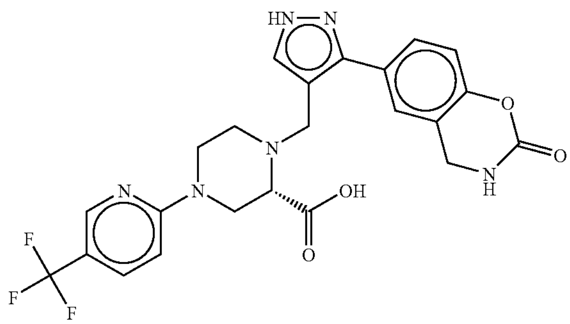 | 503.2 |
| 38 | 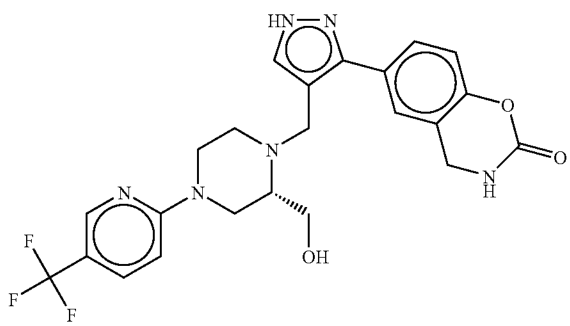 | 489.2 |
| 39 | 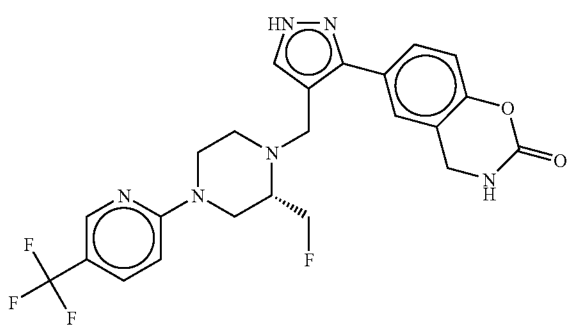 | 491.2 |
| 40 | 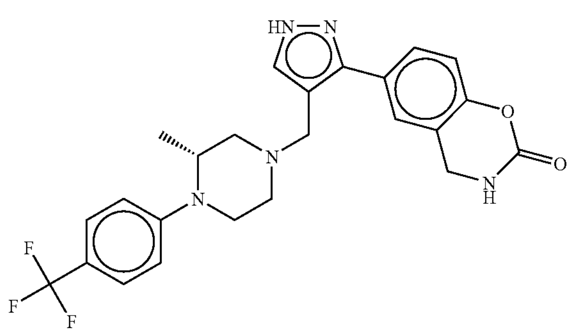 | 472.2 |

TABLE 1-continued
| Compound Number | Structure | Physical Data MS (m/z): (M + 1) |
|---|---|---|
| 41 | 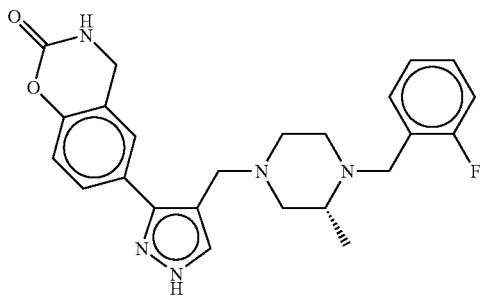 | 436.2 |
| 42 | 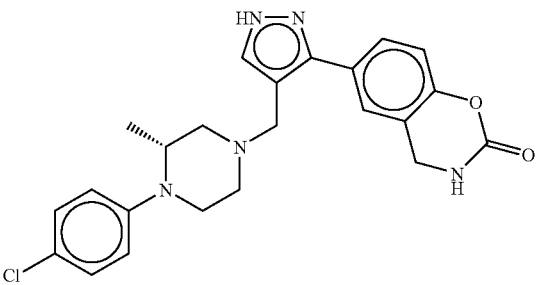 | 438.2 |
| 43 | 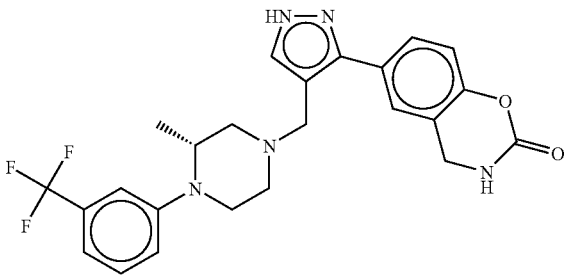 | 472.2 |
| 44 | 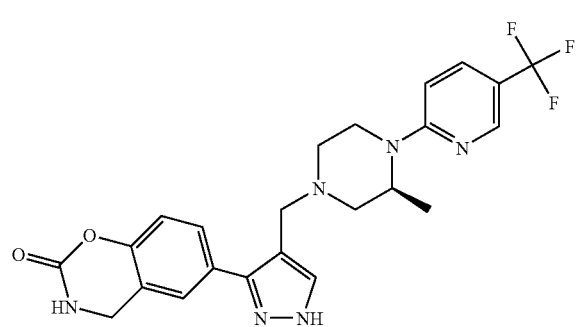 | 473.2 |
| 45 | 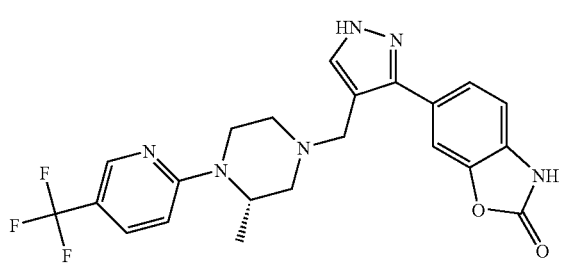 | 459.2 |

Assays

Compounds of the present invention are assayed to measure their capacity to inhibit ITPKb according to the following assays:

Purification of ITPKb: The DNA sequence encoding murine ITPKb residues 640-942 is amplified from a full-length construct in mammalian expression vector pKDNZ by PCR. The 3'-primer incorporates a stop codon and an overhanging PacI site. The product is digested with PacI before being ligated into the MH4 plasmid which has been prepared by digestion with Pm1I and PacI. Cloning into the MH4 plasmid adds the sequence MGSDKIHHHHHH to the N-terminus of the translated region. Mutant enzymes are made by site-directed mutagenesis using the Stratagene Quikchange kit.

ITPKb is expressed in the HK100 strain of *Escherichia coli*. Typically, a 4 L batch of cells is grown in LB with 0.1 μg/mL ampicillin to 0.5 $A_{600}$ at 30 degrees C., before induction with 0.02% L-arabinose for 6 hours. Cells are harvested by centrifugation, and pellets are resuspended in 50 mL of 50 mM Tris (pH 8), 100 mM NaCl, 1 mM TCEP, and 0.1 mg/mL lysozyme, with 1 Complete protease inhibitor tablet (Roche). Cells are disrupted by sonication, and debris is removed by centrifugation for 40 minutes at 35000 g.

Initial purification is performed using three nickel-Sepharose Hi-Trap HP 1 mL columns (Amersham) connected in series. After application of the pellet supernatants, the bound material is washed with 20 mM Tris (pH 8.0), 20 mM imidazole, 10% glycerol (v/v), and 1 mM TCEP before elution with an imidazole gradient up to 200 mM.

Fractions containing ITPKb are identified by SDS-PAGE, and the pure fractions ae concentrated and buffer exchanged using centriprep 20 15 kDa columns into 20 mM Tris (pH 8), 200 mM KCl, 5 mM $MgCl_2$, 0.5 mM DTT, 10% glycerol, 1 μM $IP_3$, and 20 μM ATP to a final protein concentration of 7 mg/mL.

Biochemical Measurement of ITPKb Activity: ITPKb activity is determined using the Kinase-Glo (Promega) ATP depletion assay. The assay reaction buffer consists of 50 mM Tris (pH 8.0), 100 mM NaCl, 1 mM DTT, 10% glycerol, 5 mM $MgCl_2$, 1 μM ATP, and 10 μM $IP_3$ (Alexis Biochemicals). 50 nl of inhibitor is then added to each 40 μL reaction followed by a 10 μL addition of purified ITPKb (final concentration of 60 nM). The reaction mixture is incubated for 60 minutes at room temperature and stopped by the addition of an equal volume of kinase-glo reagent (Promega). Luminescence is measured using a Molecular Devices Acquest instrument.

Compounds of Formula I preferably have an $IC_{50}$ of less than 500 nM, preferably less than 250 nM, more preferably less than 100 nM at inhibiting the phosphorylation of IP3.

Measuring Intracellular IP3, IP4, and IP5 levels by HPLC: Jurkat cells are obtained from ATCC (clone E6-1) (www.ATCC.org Cat#TIB-152). $10^7$ cells in 1 ml of inositol free RPMI-1640 w/o serum, are pulse labeled at 37° C. for 6 hours with 15 uCi of 3H myo-inositol in inositol. Cells are then diluted to 4 ml of RPMI-1640 with 10% FBS and incubated overnight at 37° C. Cells are then concentrated and resuspended in 1 ml of RPMI-1640 w/10% FBS. 1 μl of inhibitor in DMSO is then added. 50 μg of OKT3 and 10 μg of anti-human CD28 (BD Pharmingen clone CD28.2) is added followed by a 5 minute incubation at 37° C. Cells are then concentrated and the reaction quenched with the resuspension of the cell pellet in 100 μL of PBS w/350 mM HCl. Extracts are then spun to remove proteins and cellular debris. Labeled inositol polyphosphates in the extracts are then resolved by HPLC on a Partisphere SAX column (15 cm×4.6 mm) Samples are eluted as follows with gradients generated by mixing buffer A (10 mM $(NH_4)H_2PO_4$, pH 3.35, with $H_3PO_4$) with buffer B (1.7 M $(NH_4)H_2PO_4$, pH 3.35, with $H_3PO_4$). 0-12.5 minutes 0-100% Buffer B; 12-5-25 minutes 100% Buffer B; 25-30 minutes 0-100% buffer A; 30-45 minutes 100% buffer A. Radioactivity is detected with an online β-Ram detector from IN/US systems.

Compounds of Formula I preferably have an $IC_{50}$ of less than 1 μM, more preferably less than 500 nM in inhibiting the conversion of IP3 to IP4.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

We claim:
1. A compound of Formula I:

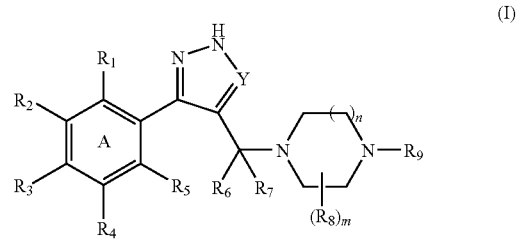

wherein:
n is 1;
m is selected from 0, 1, 2 and 3;
up to 3 groups of Ring A selected from —$CR_1$=, —$CR_2$= and —$CR_5$= are optionally replaced with —N=;
$R_1$, $R_2$ and $R_5$ are independently selected from hydrogen, hydroxy, halo, cyano, $C_{1-6}$alkyl, halo-substituted-$C_{1-6}$alkyl, hydroxy-substituted-$C_{1-6}$alkyl and cyano-substituted-$C_{1-6}$alkyl;
$R_3$ and $R_4$, together with the carbon atoms to which $R_3$ and $R_4$ are attached, form a 5 to 6 member heterocycle fused to ring A containing up to 4 radicals selected from O, C(O), S(O)$_2$, $CR_{11}R_{12}$ and NH; wherein each $R_{11}$ and $R_{12}$ are independently selected from hydrogen, $C_{1-3}$alkyl, and halo-substituted-$C_{1-3}$alkyl; or $R_{11}$ and $R_{12}$, together with the carbon to which they are both attached, forms $C_{3-7}$cycloalkyl;
$R_6$ and $R_7$ are independently selected from hydrogen, $C_{1-3}$alkyl and halo-substituted-$C_{1-3}$alkyl; or $R_6$ and $R_7$, together with the carbon to which they are both attached, forms $C_{3-7}$cycloalkyl;
$R_8$ is selected from $C_{1-6}$alkyl, $C_{2-6}$alkenyl, halo-substituted-$C_{1-6}$alkyl and hydroxy-substituted-$C_{1-6}$alkyl; or two $R_8$ groups can combine to form an alkyl bridge; or when two $R_8$ groups are attached to the same carbon atom, they, together with the carbon to which they are both attached, form $C_{3-7}$cycloalkyl;
$R_9$ is selected from $L_1$-$C_{6-10}$aryl, $L_1$-$C_{1-10}$heteroaryl, $C_{1-6}$alkyl, $L_1$-$C_{3-12}$cycloalkyl and $L_1$-$C_{3-8}$heterocycloalkyl; wherein said aryl, heteroaryl, cycloalkyl and heterocycloalkyl of $R_9$ can be optionally substituted with 1 to 3 radicals independently selected from halo, cyano, hydroxy, $C_{1-3}$alkyl, halo-substituted-$C_{1-3}$alkyl, cyano-substituted-$C_{1-3}$alkyl, hydroxy-substituted-$C_{1-3}$alkyl, —C(O)$R_{13}$, —C(O)N$R_{13}R_{14}$; wherein each $R_{13}$ and $R_{14}$ are independently selected from hydrogen and $C_{1-6}$alkyl;

$L_1$ is a bond, $C_{1-3}$alkyl or halo-substituted-$C_{1-3}$alkyl;

Y is N or $CR_{10}$;

$R_{10}$ is selected from hydrogen, $C_{1-6}$alkyl, —N$R_{15}R_{16}$, —N$R_{15}$C(O)$R_{16}$ and —C(O)N$R_{15}R_{16}$; wherein each $R_{15}$ and $R_{16}$ are independently selected from hydrogen, $C_{1-6}$alkyl, $C_{6-10}$aryl, $C_{1-10}$heteroaryl, $C_{3-12}$cycloalkyl and $C_{3-8}$heterocycloalkyl; wherein said aryl, heteroaryl, cycloalkyl and heterocycloalkyl can be optionally substituted with 1 to 3 radicals independently selected from halo, hydroxy, cyano, $C_{1-6}$alkyl, halo-substituted-$C_{1-6}$alkyl, $C_{1-6}$alkoxy and halo-substituted-$C_{1-6}$alkoxy;

and the pharmaceutically acceptable salts thereof.

2. The compound of claim 1, wherein:

n is 1;

m is selected from 0, 1 and 2;

up to 3 groups of Ring A selected from —$CR_1$=, —$CR_2$= and —$CR_5$= are optionally replaced with —N=

$R_1$, $R_2$ and $R_5$ are hydrogen;

$R_6$ and $R_7$ are hydrogen;

$R_8$ is selected from $C_{1-6}$alkyl, halo-substituted-$C_{1-6}$alkyl and hydroxy-substituted-$C_{1-6}$alkyl; or two $R_8$ groups can combine to form an alkyl bridge; or when two $R_8$ groups are attached to the same carbon, they, together with the carbon to which they are both attached, form $C_{3-7}$cycloalkyl;

$R_9$ is selected from $L_1$-$C_{6-10}$aryl, $L_1$-$C_{1-10}$heteroaryl, $C_{1-6}$alkyl, $L_1$-$C_{3-12}$cycloalkyl and $L_1$-$C_{3-8}$heterocycloalkyl; wherein said aryl, heteroaryl, cycloalkyl and heterocycloalkyl of $R_9$ can be optionally substituted with 1 to 3 radicals independently selected from halo, cyano, hydroxy, $C_{1-3}$alkyl, halo-substituted-$C_{1-3}$alkyl, cyano-substituted-$C_{1-3}$alkyl, hydroxy-substituted-$C_{1-3}$alkyl, —C(O)$R_{13}$, —C(O)N$R_{13}R_{14}$; wherein each $R_{13}$ and $R_{14}$ are independently selected from hydrogen and $C_{1-6}$alkyl;

$L_1$ is a bond or $C_{1-3}$alkyl;

Y is $CR_{10}$, and $R_{10}$ is hydrogen.

3. The compound of claim 2, wherein the 5 to 6 member heterocycle fused to ring A formed from $R_3$ and $R_4$, together with the carbon atoms to which $R_3$ and $R_4$ are attached, is selected from:

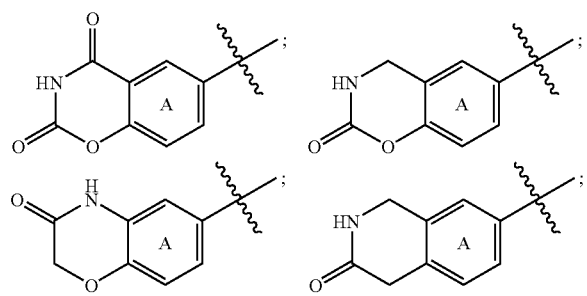

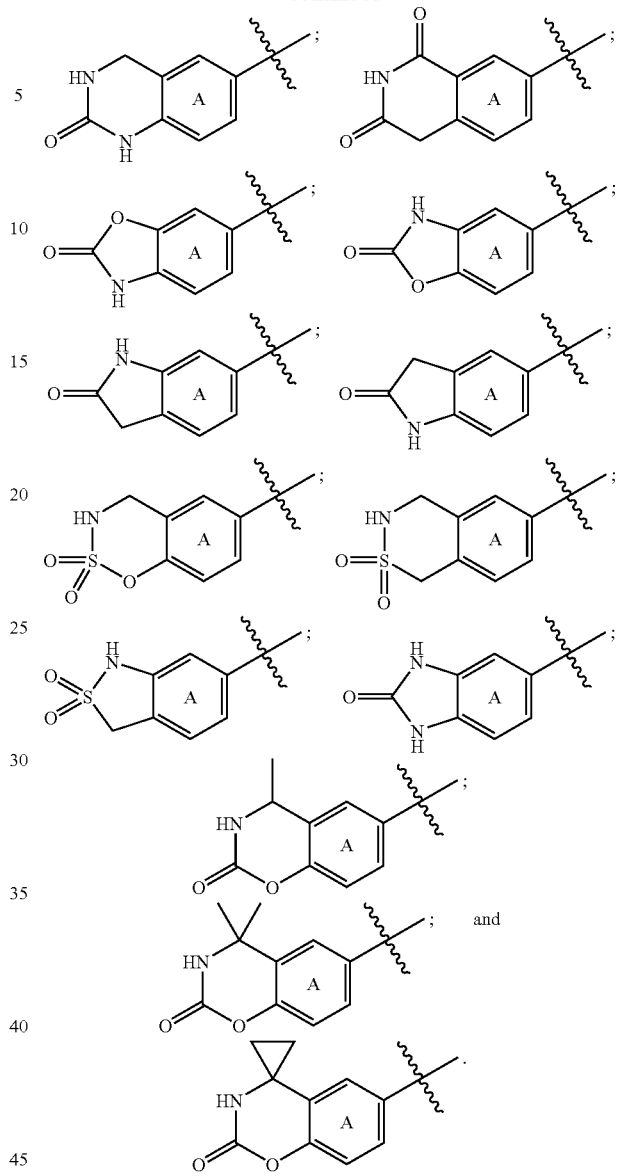

4. The compound of claim 3, wherein $R_8$ is selected from methyl, ethyl, trifluoromethyl, difluoromethyl, fluoromethyl and hydroxy-methyl; or two $R_8$ groups can combine to form an alkyl bridge selected from methyl, ethyl and propyl; or two $R_8$ groups are attached to the same carbon, they, together with the carbon to which they are both attached, form cyclopropyl.

5. The compound of claim 4, wherein $R_9$ is selected from $C_{3-7}$cycloalkyl, $C_{4-7}$heterocycloalkyl, phenyl, pyridinyl, pyrazinyl, pyrimidinyl and furo[3,2-c]pyridin-4-yl; wherein said phenyl, pyridinyl, pyrazinyl, pyrimidinyl or furo[3,2-c]pyridin-4-yl is optionally substituted with 1 to 3 radicals independently selected from trifluoromethyl, cyano, bromo, chloro, hydroxy-methyl, methyl-carbonyl, methyl, amino-carbonyl, nitro, iodo, fluoro, methoxy-carbonyl, hydroxy, amino, carboxy and methoxy.

6. The compound of claim 1 selected from: 6-(4-((4-(5-(trifluoromethyl)pyridin-2-yl)piperazin-1-yl)methyl)-1H-pyrazol-3-yl)-3H-benzo[e][1,3]oxazine-2,4-dione; 6-(4-(((R)-4-(5-(trifluoromethyl)pyridin-2-yl)-3-methylpiperazin-1-yl)methyl)-1H-pyrazol-3-yl)-3H-benzo

[e][1,3]oxazine-2,4-dione; 6-(4-(((S)-4-(5-(trifluoromethyl)pyridin-2-yl)-3-methylpiperazin-1-yl)methyl)-1H-pyrazol-3-yl)-3H-benzo[e][1,3]oxazine-2,4-dione; 6-(4-(((R)-4-(5-(trifluoromethyl)pyridin-2-yl)-3-methylpiperazin-1-yl)methyl)-1H-pyrazol-3-yl)-3,4-dihydrobenzo[e][1,3]oxazin-2-one; 7-(4-(((R)-4-(5-(trifluoromethyl)pyridin-2-yl)-3-methylpiperazin-1-yl)methyl)-1H-pyrazol-3-yl)-1,2-dihydroisoquinolin-3(4H)-one; 7-(4-(((R)-4-(5-(trifluoromethyl)pyridin-2-yl)-3-methylpiperazin-1-yl)methyl)-1H-pyrazol-3-yl)isoquinoline-1,3(2H,4H)-dione; 6-(4-(((R)-4-(5-(trifluoromethyl)pyridin-2-yl)-3-methylpiperazin-1-yl)methyl)-1H-pyrazol-3-yl)-3,4-dihydroquinazolin-2(1H)-one; (R)-6-(4-((3-methyl-4-(5-(trifluoromethyl)pyridin-2-yl)piperazin-1-yl)methyl)-1H-pyrazol-3-yl)benzo[d]oxazol-2(3H)-one; 6-(4-((3-(trifluoromethyl)-4-(5-(trifluoromethyl)pyridin-2-yl)piperazin-1-yl)methyl)-1H-pyrazol-3-yl)-3,4-dihydro-2H-benzo[e][1,3]oxazin-2-one; 6-(4-((4-(5-(trifluoromethyl)pyridin-2-yl)piperazin-1-yl)methyl)-1H-pyrazol-3-yl)-3,4-dihydro-2H-benzo[e][1,3]oxazin-2-one; (R)-5-(4-((3-methyl-4-(5-(trifluoromethyl)pyridin-2-yl)piperazin-1-yl)methyl)-1H-pyrazol-3-yl)benzo[d]oxazol-2(3H)-one; 6-(4-((3-(5-(trifluoromethyl)pyridin-2-yl)-3,6-diazabicyclo[3.1.1]heptan-6-yl)methyl)-1H-pyrazol-3-yl)-3,4-dihydro-2H-benzo[e][1,3]oxazin-2-one; 6-(4-((2-(trifluoromethyl)-4-(5-(trifluoromethyl)pyridin-2-yl)piperazin-1-yl)methyl)-1H-pyrazol-3-yl)-3,4-dihydro-2H-benzo[e][1,3]oxazin-2-one; 6-(4-((3-(5-(trifluoromethyl)pyridin-2-yl)-3,8-diazabicyclo[3.2.1]octan-8-yl)methyl)-1H-pyrazol-3-yl)-3,4-dihydro-2H-benzo[e][1,3]oxazin-2-one; 6-(4-((3-(5-(trifluoromethyl)pyridin-2-yl)-3,8-diazabicyclo[3.2.1]octan-8-yl)methyl)-1H-pyrazol-3-yl)-3,4-dihydro-2H-benzo[e][1,3]oxazin-2-one; 6(4-((3-(5-(trifluoromethyl)pytidin-2-yl)-3,8-diazabicyclo[3.2.1]octan-8-yl)methyl)-1H-pyrazol-3-yl)-2H -benzo[e][3]oxazine-2,4(3H)-dione; (S)-6-(4-((3-(fluoromethyl)-4-(5-(trifluoromethyl)pyridin-2-yl)piperazin-1-yl)methyl)-1H-pyrazol-3-yl)-3,4-dihydro-2H-benzo[e][1,3]oxazin-2-one; 6-(4-((4-(2,3-dimethylphenyl)piperazin-1-yl)methyl)-1H-pyrazol-3-yl)-2H-benzo[e][1,3]oxazine-2,4(3H)-dione; 6-(4-((4-(5-(trifluoromethyl)pyridin-2-yl)piperazin-1-yl)methyl)-1H-pyrazol-3-yl)-2H-benzo[b][1,4]oxazin-3(4H)-one; 6-(4-((4-(2,3-dimethylphenyl)piperazin-1-yl)methyl)-1H-pyrazol-3-yl)benzo[d]oxazol-2(3H)-one; (S)-6-(4-((3-(trifluoromethyl)-4-(5-(trifluoromethyl)pyridin-2-yl)piperazin-1-yl)methyl)-1H-pyrazol-3-yl)-3,4-dihydro-2H-benzo[e][1,3]oxazin-2-one; (R)-6-(4-((3-(trifluoromethyl)-4-(5-(trifluoromethyl)pyridin-2-yl)piperazin-1-yl)methyl)-1H-pyrazol-3-yl)-3,4-dihydro-2H-benzo[e][1,3]oxazin-2-one; (S)-6-(4-((3-(hydroxymethyl)-4-(5-(trifluoromethyl)pyridin-2-yl)piperazin-1-yl)methyl)-1H-pyrazol-3-yl)-3,4-dihydro-2H-benzo[e][1,3]oxazin-2-one; (R)-2-(2-methyl-4-((3-(2-oxo-3,4-dihydro-2H-benzo[e][1,3]oxazin-6-yl)-1H-pyrazol-4-yl)methyl)piperazin-1-yl)isonicotinonitrile; (R)-6-(4-((3-methyl-4-(4-(trifluoromethyl)pyrimidin-2-yl)piperazin-1-yl)methyl)-1H-pyrazol-3-yl)-3,4-dihydro-2H-benzo[e][1,3]oxazin-2-one; (R)-6-(4-((3-methyl-4-(5-methylpyridin-2-yl)piperazin-1-yl)methyl)-1H-pyrazol-3-yl)-3,4-dihydro-2H-benzo[e][1,3]oxazin-2-one; (S)-6-(4-((3-methyl-4-(5-(trifluoromethyl)pyridin-2-yl)piperazin-1-yl)methyl)-1H-pyrazol-3-yl)-3,4-dihydro-2H-benzo[e][1,3]oxazin-2-one; (R)-6-(4-((4-cyclohexyl-3-methylpiperazin-1-yl)methyl)-1H-pyrazol-3-yl)-3,4-dihydro-2H-benzo[e][1,3]oxazin-2-one; (R)-6-(5-((3-methyl-4-(5-(trifluoromethyl)pyridin-2-yl)piperazin-1-yl)methyl)-2H-1,2,3-triazol-4-yl)-3,4-dihydro-2H-benzo[e][1,3]oxazin-2-one; (R)-4,4-dimethyl-6-(4-((3-methyl-4-(5-(trifluoromethyl)pyridin-2-yl)piperazin-1-yl)methyl)-1H-pyrazol-3-yl)-3,4-dihydro-2H-benzo[e][1,3]oxazin-2-one; 6-(4-((4-(5-(trifluoromethyl)pyridin-2-yl)-4,7-diazaspiro[2.5]octan-7-yl)methyl)-1H-pyrazol-3-yl)-3,4-dihydro-2H-benzo[e][1,3]oxazin-2-one; (R)-6-(2-methyl-4-((3-(2-oxo-3,4-dihydro-2H-benzo[e][1,3]oxazin-6-yl)-1H-pyrazol-4-yl)methyl)piperazin-1-yl)nicotinonitrile; (R)-6-(4-((4-(5-chloropyridin-2-yl)-3-methylpiperazin-1-yl)methyl)-1H-pyrazol-3-yl)-3,4-dihydro-2H-benzo[e][1,3]oxazin-2-one; (S)-1-((3-(2-oxo-3,4-dihydro-2H-benzo[e][1,3]oxazin-6-yl)-1H-pyrazol-4-yl)methyl)-4-(5-(trifluoromethyl)pyridin-2-yl)piperazine-2-carboxylic acid; (S)-6-(4-((2-(hydroxymethyl)-4-(5-(trifluoromethyl)pyridin-2-yl)piperazin-1-yl)methyl)-1H-pyrazol-3-yl)-3,4-dihydro-2H-benzo[e][1,3]oxazin-2-one; (S)-6-(4-((2-(fluoromethyl)-4-(5-(trifluoromethyl)pyridin-2-yl)piperazin-1-yl)methyl)-1H-pyrazol-3-yl)-3,4-dihydro-2H-benzo[e][1,3]oxazin-2-one; (R)-6-(4-((3-methyl-4-(4--(trifluoromethyl)phenyl)piperazin-1-yl)methyl)-1H-pyrazol-3-yl)-3,4-dihydro-2H-benzo[e][1,3]oxazin-2-one; (R)-6-(4-((4-(2-fluorobenzyl)-3-methylpiperazin-1-yl)methyl)-1H-pyrazol-3-yl)-3,4-dihydro-2H-benzo[e][1,3]oxazin-2-one; (R)-6-(4-((4-(4-chlorophenyl)-3-methylpiperazin-1-yl)methyl)-1H-pyrazol-3-yl)-3,4-dihydro-2H-benzo[e][1,3]oxazin-2-one; (R)-6-(4-((3-methyl-4-(5-(trifluoromethyl)pyridin-2-yl)piperazin-1-yl)methyl)-1H-pyrazol-3-yl)-3,4-dihydro-2H-benzo[e][1,3]oxazin-2-one; (S)-6-(4-((3-methyl-4-(5-(trifluoromethyl)pyridin-2-yl)piperazin-1-yl)methyl)-1H-pyrazol-3-yl)-3,4-dihydro-2H-benzo[e][1,3]oxazin-2-one; (S)-6-(4-((3-methyl-4-(5-(trifluoromethyl)pyridin-2-yl)piperazin-1-yl)methyl)-1H-pyrazol-3-yl)benzo[d]oxazol-2(3H)-one, and (R)-6-(4-((3-methyl-4-(3-(trifluoromethyl)phenyl)piperazin-1-yl)methyl)-1H-pyrazol-3-yl)-3,4-dihydro-2H-benzo[e][1,3]oxazin-2-one; (S)-6-(4-((4-cyclohexyl-3-methylpiperazin-1-yl)methyl)-1H-pyrazol-3-yl)-3,4-dihydro-2H-benzo[e][1,3]oxazin-2-one.

7. A method for modulating B lymphocyte development and function in a subject for the treatment of autoimmune diseases, the method comprising administering to the subject a pharmaceutical composition comprising an effective amount of a compound of Formula I according to claim 1 which modulates the kinase activity or cellular level of an ITPKb molecule; thereby modulating B lymphocyte differentiation and function in a subject and wherein the autoimmune disease is selected from rheumatoid arthritis, systemic lupus erythematosus, idiopathic thrombocytopenic purpura, hemolytic anemia, and psoriasis.

\* \* \* \* \*